US012171696B1

(12) United States Patent
Panetta et al.

(10) Patent No.: US 12,171,696 B1
(45) Date of Patent: Dec. 24, 2024

(54) ARM SUPPORT ASSEMBLY FOR MEDICAL APPLICATIONS

(71) Applicant: LP Medical LLC, Minneapolis, MN (US)

(72) Inventors: Carmelo J. Panetta, Minneapolis, MN (US); Yunxing Liu, North Oaks, MN (US)

(73) Assignee: LP Medical LLC, Minneapolis, MN (US)

( * ) Notice: Subject to any disclaimer, the term of this patent is extended or adjusted under 35 U.S.C. 154(b) by 779 days.

(21) Appl. No.: 16/851,084

(22) Filed: Apr. 16, 2020

Related U.S. Application Data

(60) Provisional application No. 62/834,436, filed on Apr. 16, 2019, provisional application No. 62/881,838, filed on Aug. 1, 2019, provisional application No. 62/981,508, filed on Feb. 25, 2020.

(51) Int. Cl.
*A61G 13/12* (2006.01)
*A61B 90/00* (2016.01)

(52) U.S. Cl.
CPC .......... *A61G 13/1235* (2013.01); *A61B 90/04* (2016.02); *A61B 2090/0436* (2016.02); *A61B 2505/05* (2013.01)

(58) Field of Classification Search
CPC ............ A61B 90/04; A61B 2090/0436; A61B 2505/05; A61B 6/0428; A61G 13/1235; A61G 13/125; A61G 1/01; A61G 1/04; A61G 15/12
See application file for complete search history.

(56) References Cited

U.S. PATENT DOCUMENTS

| 2,782,427 | A | 2/1957 | Ericson |
| 3,256,880 | A | 6/1966 | Caypinar |
| 3,668,722 | A | 6/1972 | Gallant |
| 4,270,235 | A | 6/1981 | Gutmann |
| 4,369,774 | A | 1/1983 | Robbins |

(Continued)

FOREIGN PATENT DOCUMENTS

| WO | WO2004071302 | 8/2004 |
| WO | WO2018171840 | 9/2018 |

OTHER PUBLICATIONS

LP Medical LLC, photos of Left Arm Support System, prior to Apr. 16, 2019 (8 pages).

(Continued)

*Primary Examiner* — Ophelia A Hawthorne
*Assistant Examiner* — Gina McCarthy
(74) *Attorney, Agent, or Firm* — Deirdre M Kvale; DMK Intellectual Property Law PLLC

(57) ABSTRACT

A support assembly for use during a medical or surgical procedure. The support assembly includes a base structure and a support structure removably connectable to the support structure through attachment features. In illustrated embodiments, the support structure is attached to the base structure in an upright orientation to form a sideboard or guard and attached to the base structure in a horizontal orientation to form an arm support platform. In illustrated embodiment one or both of the base structure or base board and support structure include attachment features to removably connect a radiation shield for protection against radiation exposure.

15 Claims, 41 Drawing Sheets

(56) References Cited

U.S. PATENT DOCUMENTS

| | | |
|---|---|---|
| 5,228,457 A | 7/1993 | Kawamura |
| 5,485,856 A | 1/1996 | Buckland |
| 5,546,963 A | 8/1996 | Doody |
| 5,568,662 A * | 10/1996 | Gougelet ................. A61G 1/01 5/628 |
| 5,785,057 A | 7/1998 | Fischer |
| 6,003,175 A | 12/1999 | Couch |
| 6,101,650 A | 8/2000 | Omdal |
| 7,017,215 B1 | 3/2006 | Singer et al. |
| 8,286,285 B2 | 10/2012 | Mahler |
| 8,418,696 B2 | 4/2013 | Marasco |
| 10,322,052 B2 | 6/2019 | Panetta et al. |
| D862,707 S | 10/2019 | Roelse et al. |
| 10,555,830 B2 | 2/2020 | Bergenudd et al. |
| 2004/0049851 A1* | 3/2004 | Jahrling ................... A61G 1/04 5/623 |
| 2012/0131751 A1 | 5/2012 | Mahler |
| 2015/0351707 A1* | 12/2015 | Sampognaro ........ A61B 6/0428 128/877 |
| 2016/0038365 A1 | 2/2016 | Conner et al. |
| 2016/0089295 A1* | 3/2016 | Panetta .................. A61G 15/12 128/845 |

OTHER PUBLICATIONS

Adept Medical, Starsystem product brochure, prior to Apr. 16, 2019 (3 pages).

TZ Medical, Cobra Board product brochure, prior to Apr. 16, 2019 (1 pages).

\* cited by examiner

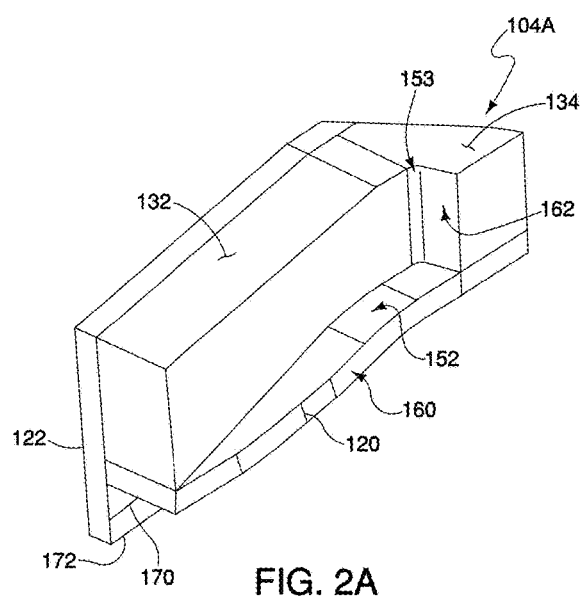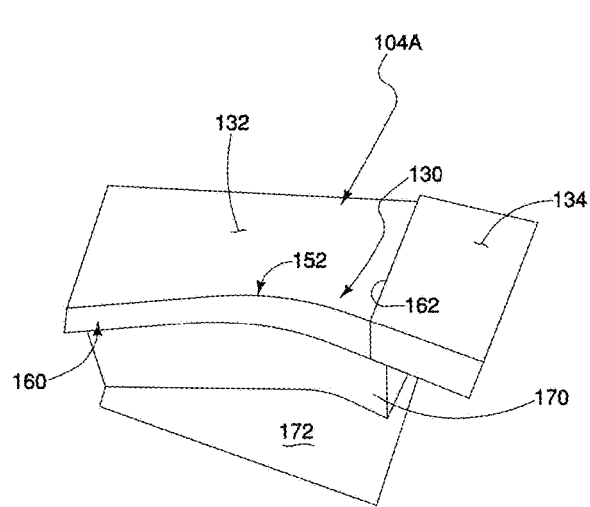
FIG. 2A
FIG. 2B

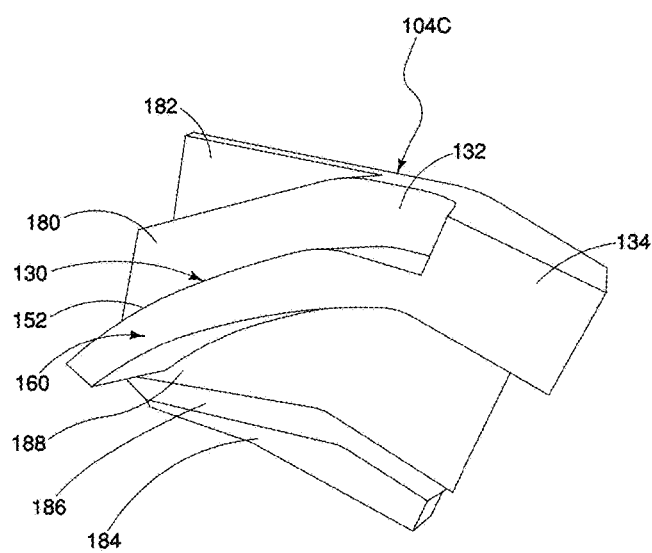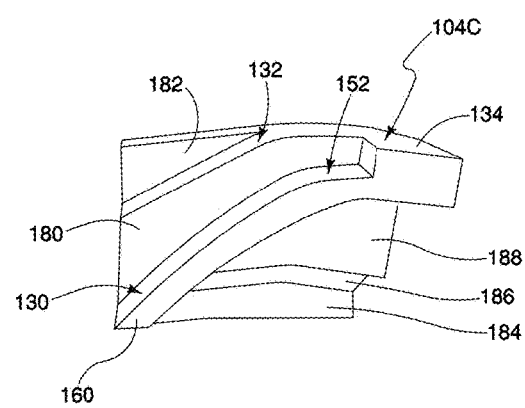
FIG. 4A
FIG. 4B

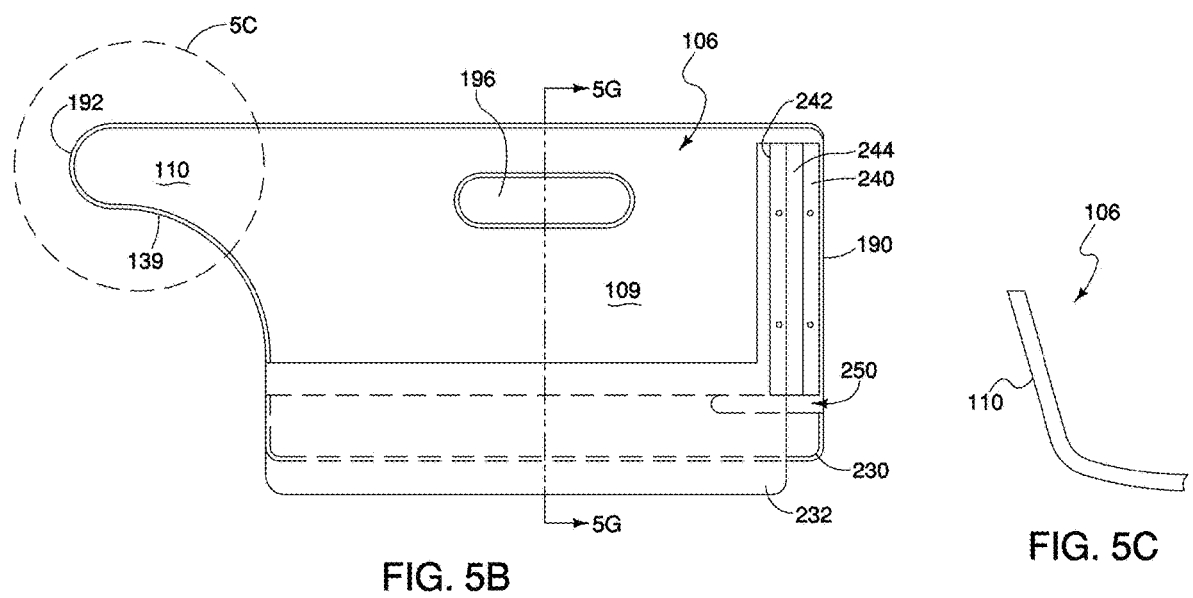

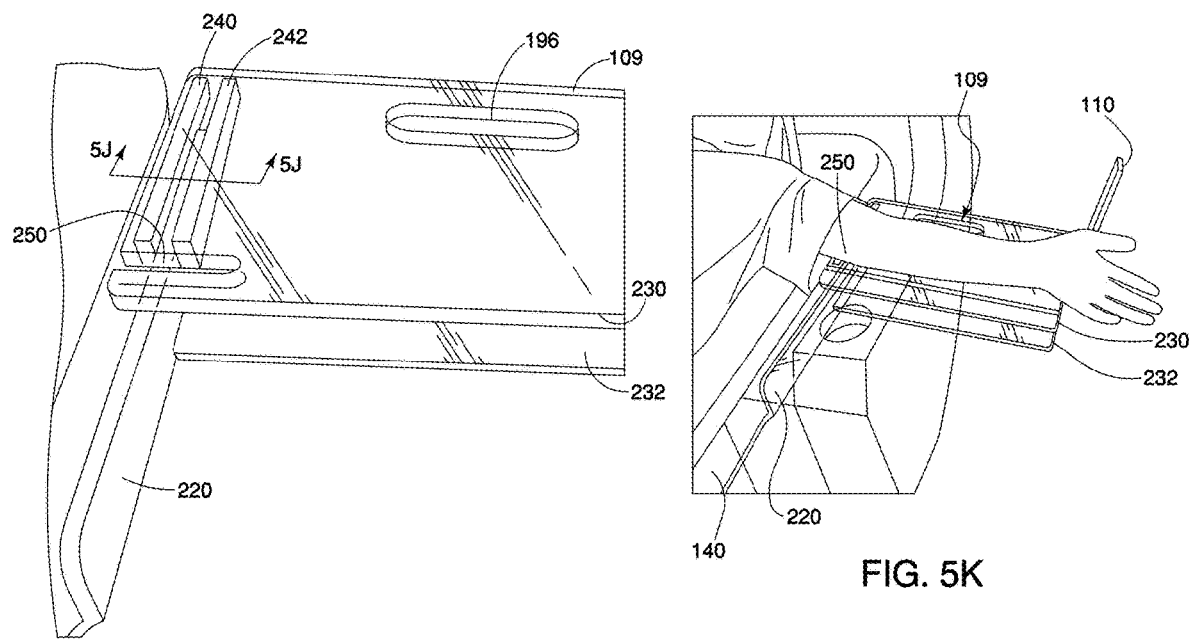

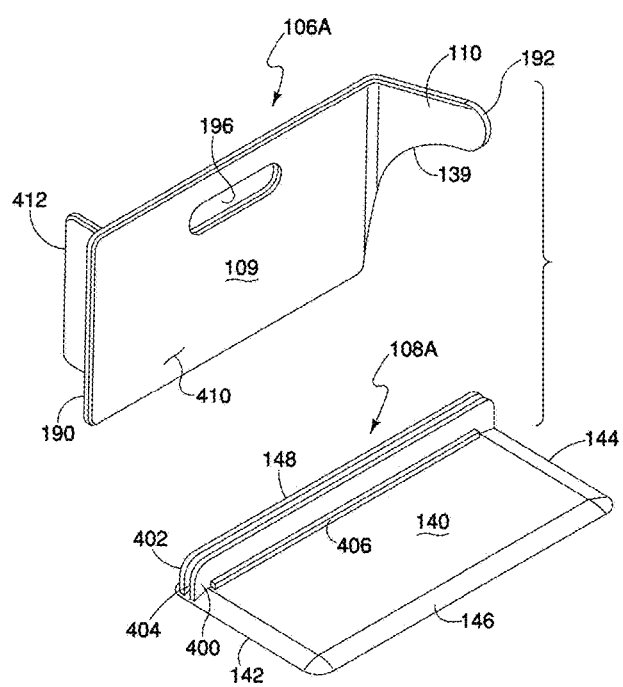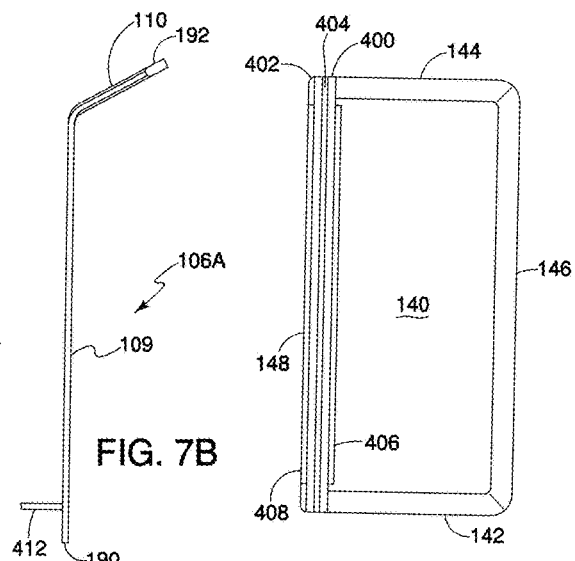
FIG. 7A
FIG. 7B
FIG. 7C

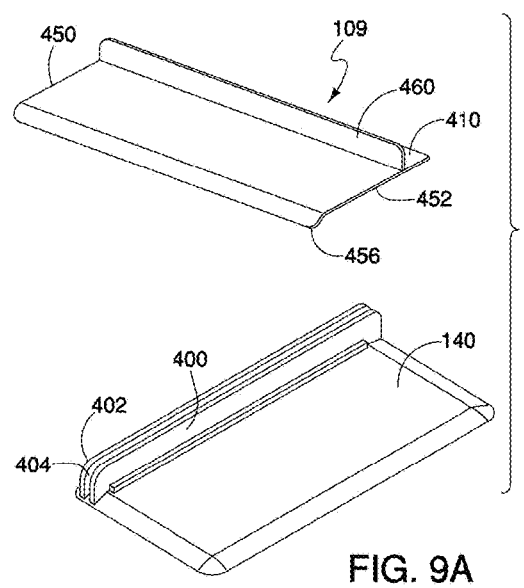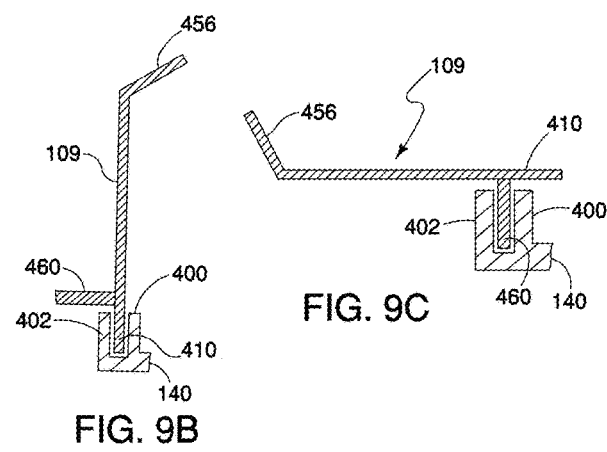
FIG. 9A
FIG. 9B
FIG. 9C

ARM SUPPORT ASSEMBLY FOR MEDICAL APPLICATIONS

CROSS-REFERENCE TO RELATED APPLICATIONS

The present application claims priority to U.S. Provisional Application Ser. No. 62/834,436 filed Apr. 16, 2019 entitled ARM SUPPORT ASSEMBLY FOR MEDICAL APPLICATIONS, U.S. Provisional Application Ser. No. 62/881,838 filed Aug. 1, 2019 and entitled ARM SUPPORT ASSEMBLY FOR MEDICAL APPLICATIONS and U.S. Provisional Application Ser. No. 62/981,508 filed Feb. 25, 2020 and entitled ARM SUPPORT WITH REMOVABLE SHIELD FOR MEDICAL APPLICATIONS, the content of which are hereby incorporated by reference into the present application in their entirety.

BACKGROUND

For medical or surgical procedures catheters or other devices may be inserted through a patient's wrist requiring access to a patient's arm during the procedure. Arm boards and other devices have been used to retain a patent's arm in a fixed position during treatment but such devices do not provide flexibility or adaptability for different procedures and applications. The present application addresses these and other issues.

SUMMARY

The present application relates to a support assembly having application for supporting a patent's arm during a medical procedure or treatment. In illustrative embodiments, the support assembly includes a base structure and an attachment removably connectable to the base structure through a base attachment feature. As disclosed the attachment includes a support structure including a first attachment feature to removably connect the support structure to the base structure in an upright orientation to form an upright arm or sideboard and a second attachment feature to removably connect the support structure to the base structure in a horizontal orientation to form a horizontal support platform. In illustrated embodiments, the assembly includes a radiation shield removably connectable to one or both of the base structure or support structure. While features or attributes are described above. The present application includes additional features and attributes as will be described in the following description and FIGS.

BRIEF DESCRIPTION OF THE DRAWINGS

FIG. 2A is a perspective illustration of an embodiment of the arm cushion of the present application.

FIG. 2B is an inner side view of the cushion of FIG. 2A.

FIGS. 4A-4B illustrate another embodiment of the cushion of the present application.

FIG. 5B is an outer side view of an embodiment of the support structure of FIG. 5A.

FIG. 5C is top view illustration of portion 5C of FIG. 5B showing a front curved portion forming the front arm extension of the side structure.

FIG. 5I illustrates the support structure of FIG. 5B connected to the base board in a back horizontal orientation to form a horizontal arm support platform.

FIG. 5K illustrates the support structure connected in the horizontal orientation to support a patient's arm as shown.

FIG. 7A is an exploded view illustrating an embodiment of a support structure or sideboard attachable to a base structure.

FIG. 7B is a top view of the support structure illustrating the curved front arm extension.

FIG. 7C is a top view of the base board including attachment rails to form a groove.

FIG. 9A is an exploded view of an embodiment of a support structure attachable to a base board of the present application.

FIG. 9B illustrates the support structure of FIG. 9A connected to the base board in an upright orientation.

FIG. 9C illustrates the support structure of FIG. 9A connected to the base board in a lengthwise horizontal orientation.

It should be noted that the above-referenced FIGS. are for illustrative purposes only and are not necessarily drawn to scale.

DETAILED DESCRIPTION OF ILLUSTRATIVE EMBODIMENTS

Figure 1A:
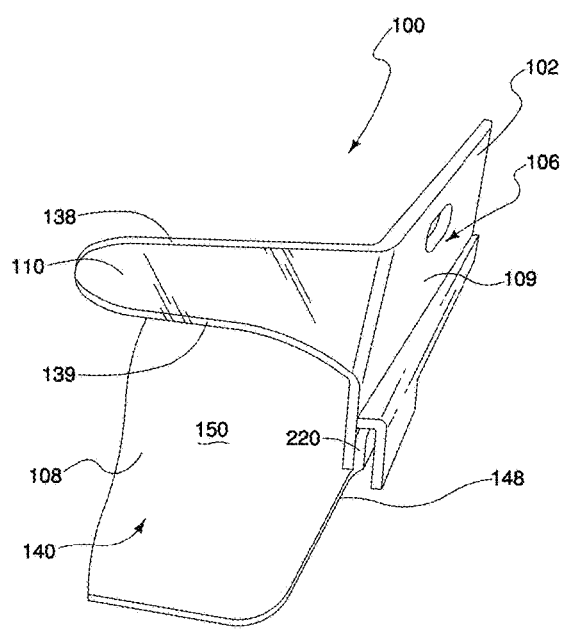
FIG. 1A is a perspective illustration of a support assembly of the present application.
Figure 1B:
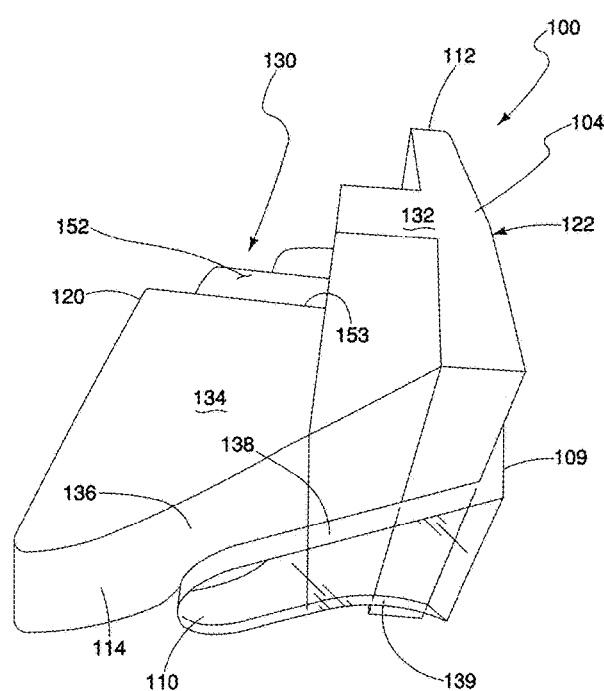
FIG. 1B is an illustration of the support assembly shown with an arm cushion in place on the support structure for use.

The present application relates to an arm support assembly 100 for supporting a human arm during a medical procedure. The assembly includes a support frame 102 and arm cushion 104 to hold the patient's arm in place as shown in FIGS. 1A-1B. The support frame 102 as shown includes a support structure 106 coupled to a base structure 108. The support structure 106 includes a flat portion 109 and front arm extension 110 angled relative to the flat portion 109 to form a sideboard attachment to hold the arm cushion 104 in place during use as shown in FIG. 1B. During use, the flat portion 109 and the front arm extension 110 engage the arm cushion 104 to limit movement (e.g. longitudinal and lateral movement) of the arm cushion 104 so that a patient's arm is steady while a medical procedure is performed.

Figure 1C:
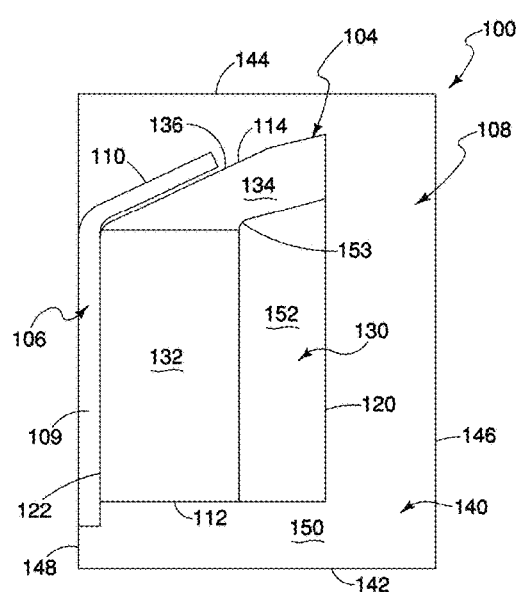
FIG. 1C is a top view of the support assembly and cushion of FIG. 1A.

The arm cushion 104 of the present application is formed of a compressible body. As shown in FIGS. 1B-1C the compressible body has an elongate length extending between a backend 112 and front end 114, and a width extending between an inner side 120 and an outer side 122. The arm cushion 104 includes an arm support feature 130, an outer side wall 132 and a front end wall 134. The arm support feature 130 extends along the inner side 120 of the cushion body from the backend 112 of the cushion 104 to the front end wall 134. The side wall 132 has an elongate length coextending along an outer edge of the arm support feature 130 to the front end wall 134. In the illustrated embodiment, the frontend wall 134 has an angled front end surface 136 configured to abut the angled front arm extension 110 as shown in FIGS. 1B-1C.

In use, the side wall 132 and frontend wall 134 of cushion 104 abut the flat portion 109 and front arm extension 110, respectively to retain the arm cushion 104 in place as previously described. In the upright position shown in FIG. 1A, the front arm extension 110 includes a top surface 138 and a bottom surface 139. The bottom surface 139 of the front arm extension 110 is elevated from the base structure 108 to align with the frontend wall 134 of the cushion 104 as shown in FIG. 1B and provide clearance for the patient's body. As shown, the bottom surface 139 of the front arm extension 110 is curved, however application is not limited to the curved bottom surface shown.

Figure 1D:
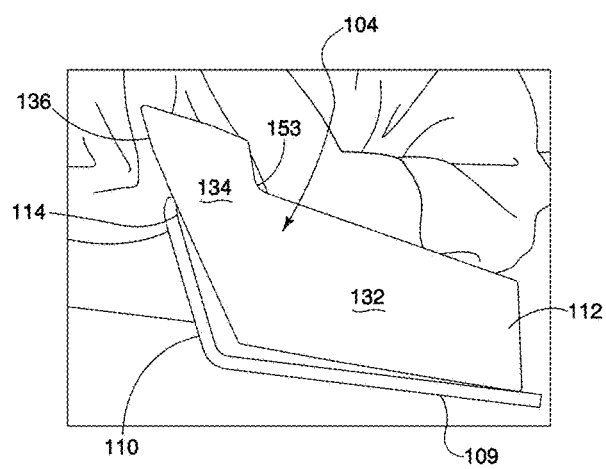
FIG. 1D is a top view of the cushion having a patient's arm resting on an arm support surface of the cushion.

In illustrated embodiments, the base structure 108 is formed of an elongate base board 140 having a length dimension extending lengthwise between a backend 142 and the front end 144 of the base board 140 and a cross width dimension between an inner edge 146 and outer edge 148 of the base board 140 as shown in FIG. 1C. The support structure 106 is coupled to the base board 140 along the outer edge 148 so that the flat portion 109 extends along the outer edge 148 and the front arm extension 110 extends laterally from the outer edge 148 in an angled direction towards the inner edge 146. The arm cushion 104 is supported on an upper surface 150 of the base board 140 alongside flat portion 109 of the support structure 106 in an upright orientation as shown in FIGS. 1C-1D. As previously described, in use the side wall 132 of the cushion 104 abuts the upright flat portion 109 and the frontend wall 134 abuts the front arm extension 110 to restrict lateral and forward movement of the arm cushion 104 as previously discussed.

In particular, the front arm extension 110 angles inwardly from flat portion 109 of the support structure 106 to restrict sliding movement of the cushion 104 away from the patient to retain the patient's arm in the desired orientation. In the illustrated embodiment, the front arm extension 110 is coupled to the flat portion 109 at an obtuse angle and the front end surface 136 of cushion 104 is orientated at an obtuse angle relative to the side wall 132, however, application is not limited to a particular embodiment or angle.

Figure 1E:
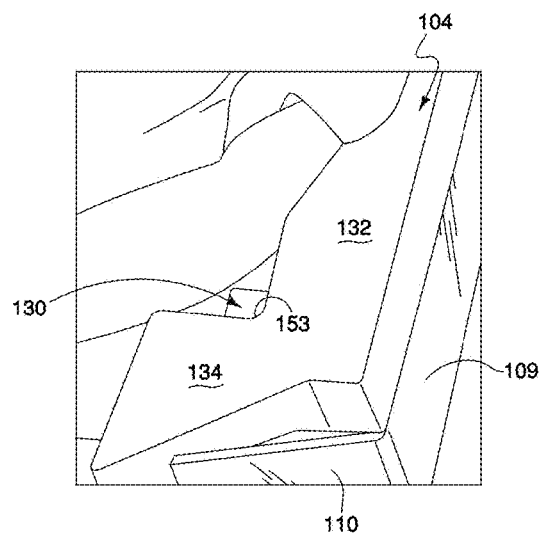
FIG. 1E illustrates a patient's arm resting on a support surface of another cushion embodiment.
Figure 1F:
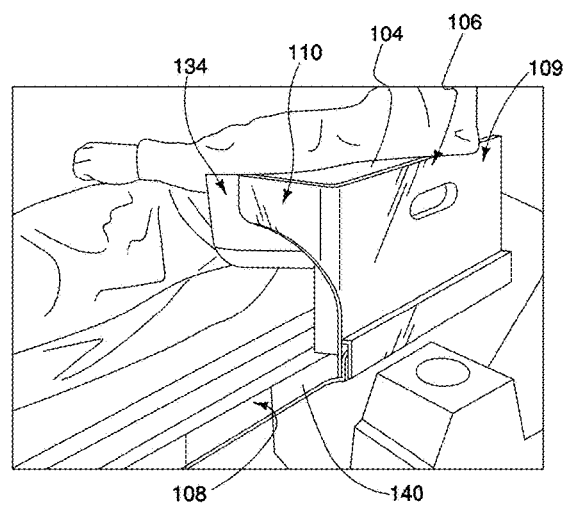
FIG. 1F illustrates the support assembly and cushion in use for a medical procedure.

The arm support feature 130 of the cushion 104 provides an arm support surface 152 along a length of the side wall 132. A length of the arm support surface 152 is sized to support the patient's upper arm. The arm support features include an elbow bend 153 at the junction of the side wall 132 and frontend wall 134 to support the patient's elbow in a bent position as shown in FIGS. 1D-1E. In particular, as shown, the bend 153 is angled to accommodate the patient's elbow in bent position for placement of the patient's forearm across the patient's abdomen while the patient's upper arm is supported along the arm support surface 152. As shown in FIG. 1F, the cushion 104 has an overall height dimension extending between a base surface 154 of the cushion 104 to a top surface 156 of the cushion 104 (FIG. 3D). For use the base board 140 is slid under the patient or hospital bed mattress M. As shown in FIG. 1F and 3D, the cushion 104 has a narrow cushion base for placement of the cushion 104 between the upright sideboard attachment or support structure 106 and mattress M.

FIGS. 2A-2D illustrates an embodiment of cushion 104A for use with the support frame 102 of the present application where like numbers are used to identify like parts as previously described. As shown, the cushion 104A is formed of a foam block structure. The foam is coated with an antimicrobial coating or sterile material for use in a sterile environment or operating room. As shown, the arm support surface 152 is formed along a sloped arm support structure 160 and extends along the inner side 120 of the cushion 104 to the frontend wall 134. An outer edge of the arm support surface 152 is bounded by side wall 132 and a forward edge extends along a backside 162 of the frontend wall 134. An inner edge of the arm support feature 130 is opened for placement of the patient's arm. The arm support surface 152 shown in FIG. 2A has a tapered back edge and rounded transition edge to follow the contour of the patient's body for placement alongside the patient's body. In the embodiment shown the sloped arm support structure 160 forms the sloped arm support surface 152 for the patient's arm. The length of the arm support surface 152 extends to bend 153. As previously described, the patient's upper arm is supported along the arm support surface 152 and the patient elbow is supported at bend 153 to position the patient's forearm across the patient's abdomen as previously described.

As shown, the cushion 104A has a narrow cushion base below the arm support structure 160. The narrow cushion base has a height sized for placement between the upright flat portion 109 of the support structure 106 and mattress M. As shown, the narrow cushion base includes wedged shaped portion 170 and an upright portion 172 below the arm support structure 160. The wedged shaped portion 170 and upright surface portion 172 are recessed from an inner side edge of the arm support structure 160 to form the narrow base width. As shown the arm support structure 160 is cantilevered relative to the narrow cushion base. The height and width (i.e. recessed dimension of the wedged shaped portion 170 and upright surface portion 172 of the cushion base are sized for placement of the cushion between the mattress M and upright flat portion 109 and sized to provide clearance for the patient's body while the patient's arm is supported on the arm support surface 152 as shown in FIG. 1F.

Figures 2C, 2D:
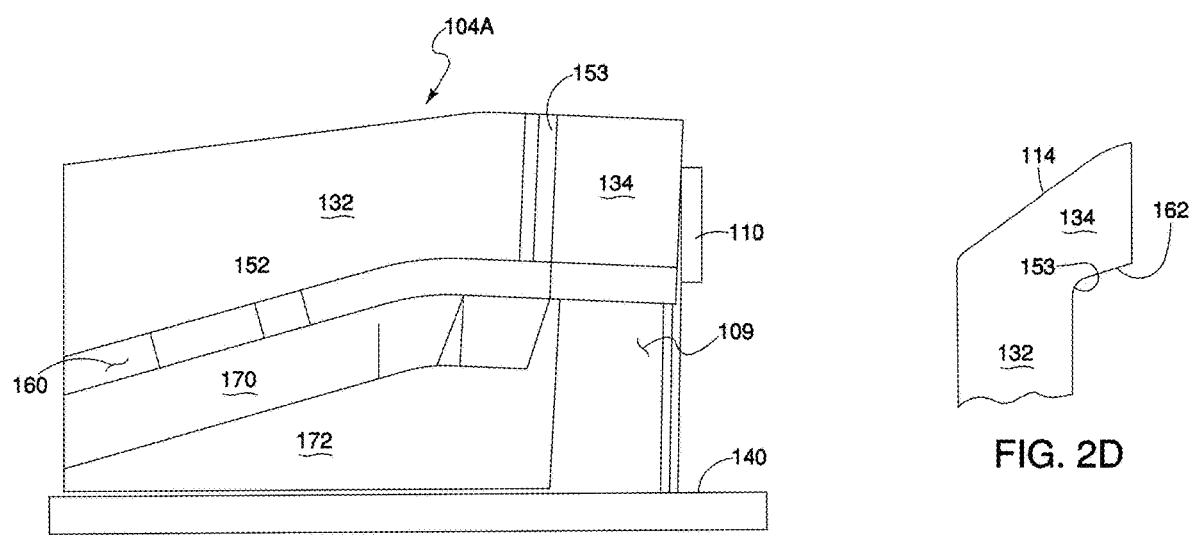
FIG. 2C is a side elevational view of an embodiment of the cushion and support assembly.
FIG. 2D illustrates a bend of an arm support feature to accommodate a patient's elbow in the bent position.

The length of the narrow cushion base extends from the back end 112 to backside 162 of the frontend wall 134 so that the frontend wall 134 is cantilevered to provide clearance between the base structure 108 and a bottom surface of the frontend wall 134. The wedged shaped portion 170 as described provides rigidity proximate to the cantilevered arm support structure 160. Similar to previous embodiments, the bend 153 at the junction of the side wall 132 and backside 162 of frontend wall 134 is angled or contoured to support a bent elbow to position the patient's forearm across the patient's abdomen as shown in FIG. 2D.

Figure 3A:
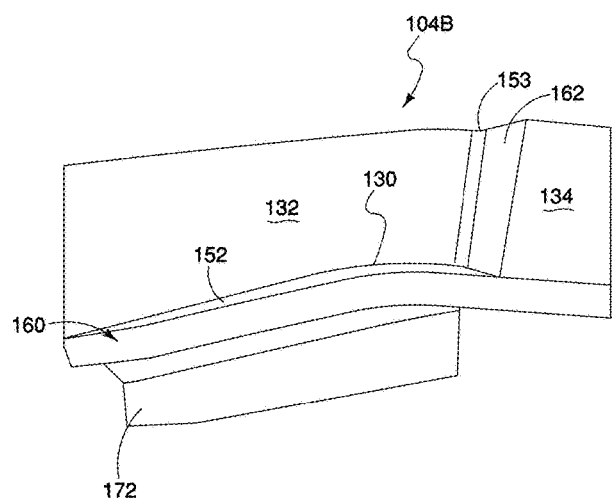
FIGS. 3A-3B illustrate an inner side of the cushion according to another embodiment.
Figure 3B:
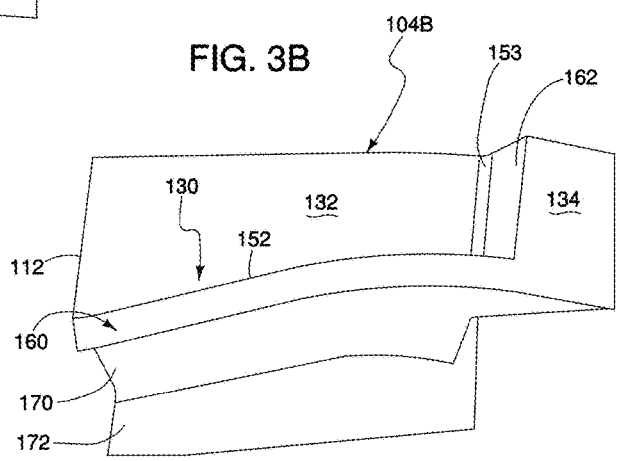
Figure 3C:
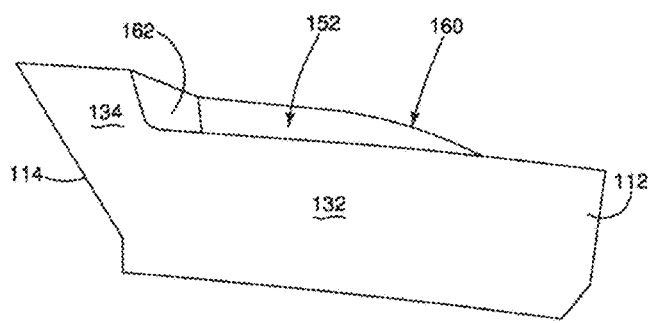
FIG. 3C is a top view of the cushion shown in FIGS. 3A-3B.
Figure 3D:
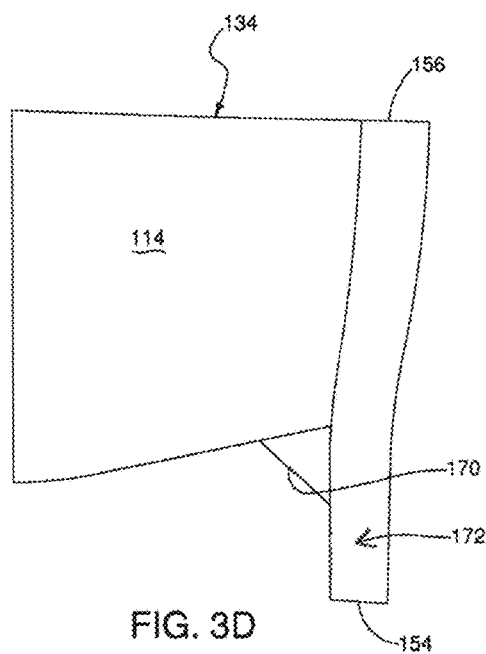
FIG. 3D is a frontend view of the cushion shown in FIGS. 3A-3B.

FIGS. 3A-3B illustrate another embodiment of the cushion 104B of the present application similar to cushion 104A where like numbers are used to refer to like parts. In the embodiment shown, the arm support structure 160 has a smaller slope angle than the embodiment illustrated in FIG. 2B and the upright portion 172 of the cushion base has a height dimension sized for placement of the cushion 104B between the flat portion 109 and mattress M for use. In particular, in an illustrated embodiment, the height of the upright portion 172 of the cushion base is 2 inches.

FIGS. 4A-4B illustrate another embodiment of a cushion 104C for use with the support frame 102 of the present application where like numbers refer to like parts in the previous figures. As shown, the arm support feature 130 is formed along the inner side 120 of the cushion 104C and includes a sloped support surface 152 along the sloped support structure 160. The sloped support surface 152 is opened along the inner side 120 of cushion 104C and closed by the side wall 132 along the outer side 122 and the frontend wall 134 along the front end 114 of cushion 104C similar to previous embodiments. The side wall 132 as shown includes stepped side wall portions 180, 182 adjacent to the arm support feature 130. The stepped side wall portions 180, 182 provide additional space to accommodate a larger sized person.

As shown the inner side wall portion 180 is sloped to provide a sloped surface adjacent to the sloped arm support surface 152. The sloped inner side wall portion 180 provides room to accommodate a patient's arm supported on the arm support structure 160. The cushion base also includes recessed portions or surfaces along the inner side below the arm support structure 160. In particular, the recessed surfaces include lower upright portion 184, a wedged shaped portion 186 and an upper upright portion 188 to form the narrow width of the cushion base. The surfaces 184, 186, 188 are recessed from the inner edge of the arm support structure 160 so that the structure is essentially cantilevered relative to the side wall 132. As shown a height of the recessed surfaces 184, 186, 188 is larger at the front end relative to the backend to accommodate the patient's body.

Figure 5A:
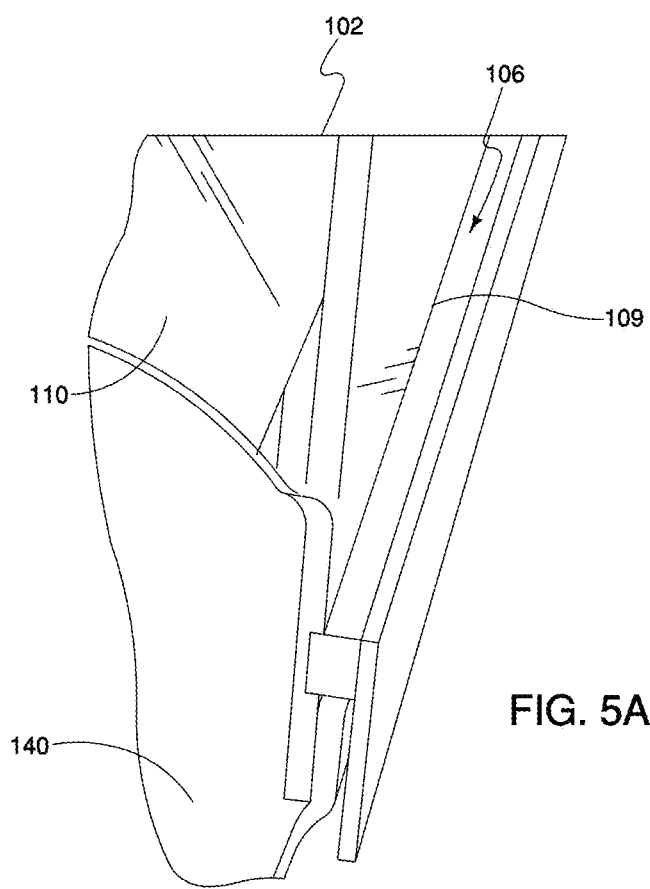
FIG. 5A is a detailed view illustrating an embodiment of the support assembly including a base board and support structure.

FIGS. 5A-5C illustrate an embodiment of the support structure 106 and base structure 108 of the present application where the support structure 106 is removably connectable to the base structure 108 or base board 140 in different orientations via attachment features on the support structure 106 and base board 140. In particular, as shown in FIGS. 5B-5C the support structure 106 includes attachment features to connect the support structure 106 to the base structure or board 140 in an upright position to support the patent's arm, for example on the cushion, in a cross abdominal position and a horizontal position to form an arm support platform as will be described herein.

In the embodiment shown in FIG. 5B, the support structure 106 has an elongate length extending from a backend 190 to front end 192 including a curved body length as shown in FIG. 5C to integrally form the flat portion 109 and front arm extension 110 angled relative to the flat portion 109. The support structure 106 includes a cut-out handle 196 formed through a thickness of the structure to manipulate the support structure 106 for connection to the base board 140 in various orientations. The bottom surface 139 of the front arm extension 110 is spaced from a bottom surface of the flat portion 109 to provide clearance for the patient's body as previously described. In particular, as previously described, the bottom surface 139 of the front arm extension 110 is curved.

Figure 5D:
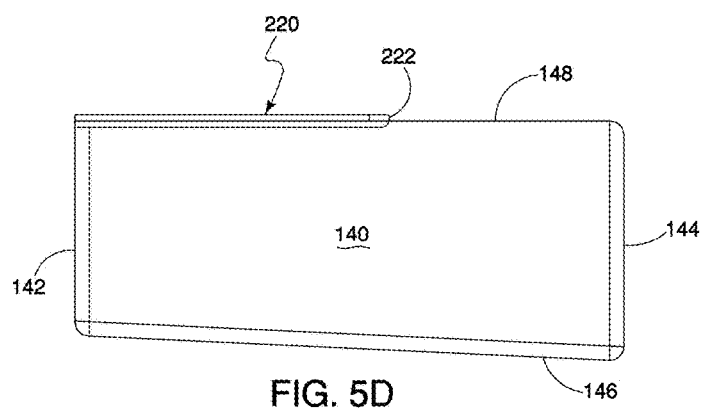
FIG. 5D is a top view of the base board of the support assembly of FIG. 5A.
Figure 5F:
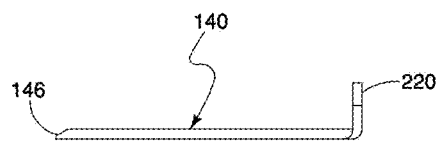
FIG. 5F is a frontend view of the base board of FIG. 5D.
Figure 5E:
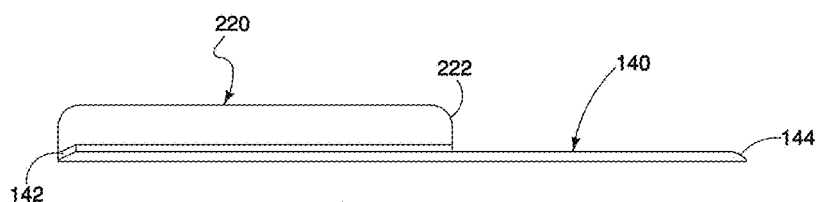
FIG. 5E is an inner side view of the base board of FIG. 5D.

FIGS. 5D-5F illustrate an embodiment of the base board 140 of an embodiment of the base structure 108 of the present application. As previously described the base board 140 has an elongate length between the backend 142 and the front end 144 and width between the inner and outer sides 146, 148. In the embodiment shown, the base board 140 includes an elongate rail 220 extending along the outer side 148 to form an attachment feature or tongue on the base board 140 to connect the support structure 106. As shown, the length of the rail 220 is shorter than the length of the base board 140 so that a front end 222 of the rail 220 is spaced from the front end 144 of the base board 140. As shown in FIG. 5D, the inner side 146 of the base board 140 is tapered to provide a narrow width dimension at the backend 142 and a larger width at the front end 144. As shown, the front, back and inner edges of the base board 140 are beveled for insertion under mattress M.

Figure 5G:
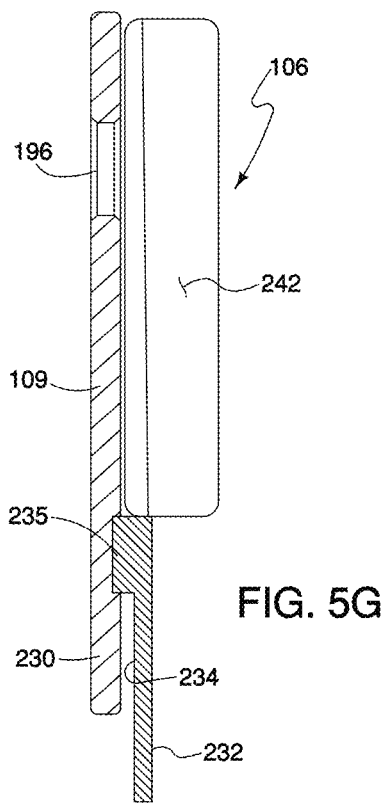
FIG. 5G is a cross-sectional view as taken along line 5G-5G of FIG. 5B.
Figure 5H:
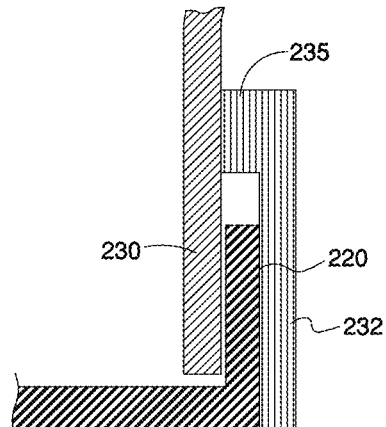
FIG. 5H is a detailed view illustrating attachment of the support structure to a base rail attachment on the base board.

FIG. 5G is a cross-sectional view generally taken along line 5G-5G of FIG. 5B of the support structure 106. As shown, the support structure 106 includes spaced attachment rails 230, 232 along a bottom edge of the flat portion 109. The rails 230, 232 are spaced to form a gap 234 or groove of an attachment feature on the support structure 106 that interfaces with the base rail 220 on the base board 140 to removably connect the support structure in an upright orientation. To connect the support structure 106 to the base board 140 in an upright position, rails 230, 232 are centered over base rail 220 so that base rail 220 is disposed in gap 234 and attachment rails 230, 232 extend alongside rail 220 to retain the support structure 106 in the upright position for use as shown in FIG. 5H. As shown, rail 230 is formed of the bottom edge of the support structure 106 and the rail 232 is formed of an elongate body connected to the support structure 106 through an elongate block 235 to form the spaced attachment rails 230, 232 as described. In an illustrated embodiment rail 232 and block 235 are glued to the support structure 106 however application is not limited to a particular attachment, for example the rail and block 235 can connected through mechanical fasteners or other attachment means.

Figure 5J:
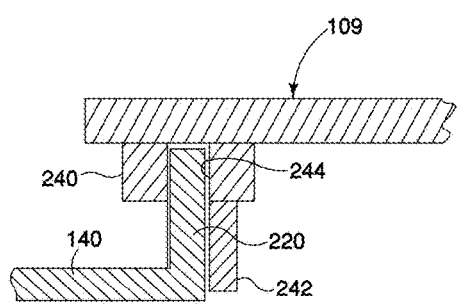
FIG. 5J is a cross-sectional view taken along line 5J-5J of FIG. 5I.

In the illustrated embodiment, the support structure 106 also includes attachment features to connect the support structure 106 to the base board 140 to form a horizontal arm support platform as shown in FIG. 5I. The attachment features include spaced back edge rails 240, 242 along the back of the support structure 106 as shown, in FIG. 5B. Rails 240, 242 are secured to an outer or lower surface of the support structure 106 via an adhesive or other connection means or device. The rails 240, 242 are spaced for placement of base rail 220 in a gap 244 between rails 240, 242 as shown in FIG. 5J to attach the support structure 106 in a horizontal support platform orientation as shown in FIG. 5I. In the embodiment shown, the rails 240, 242 extend crosswise along a cross width of the support structure 106 so that the lengthwise dimension of the support structure 106 or flat portion 109 extends outwardly from the base board or structure as shown in FIGS. 5I-5K.

The rails 240, 242 have a length that extends from a top edge of the support structure 106 to slot 250. As shown in FIG. 5I, rail 232 has a shorter length dimension (as shown in FIG. 5B) to limit interference with the base rail 220 while the support structure 106 is attached in the horizontal support platform position. As shown in FIG. 5K during use, a patient's arm extends outwardly and is supported on the horizontal support platform, for example, for inserting a catheter into a radial artery of the patient's wrist. The curved bottom surface 139 of extension 110 provides clearance for the patient's arm to allow full extension of the patient's arm.

Figure 5L:
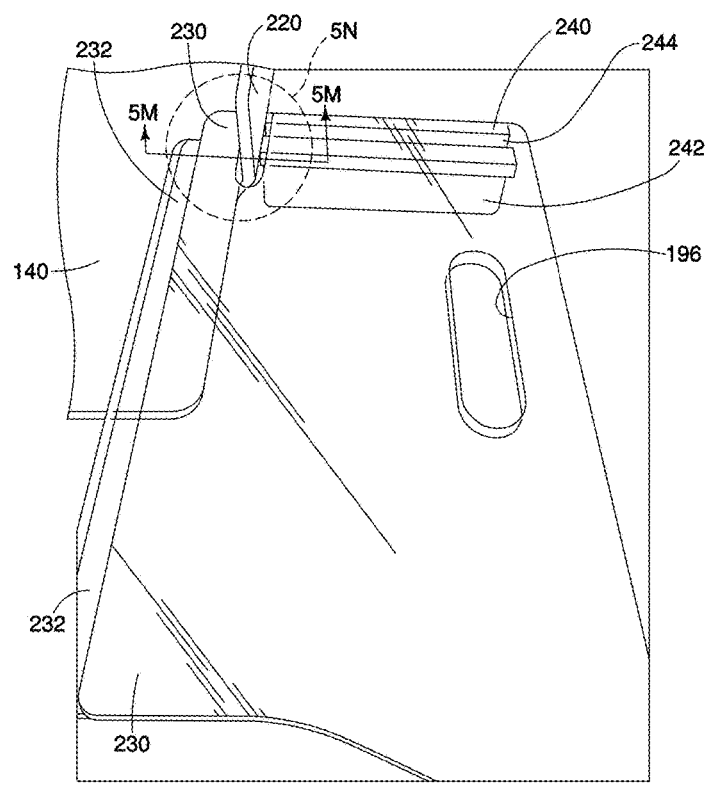
FIG. 5L illustrates the support structure of FIG. 5B connected to the base board in a horizontal position to form an arm support platform.
Figure 5N:
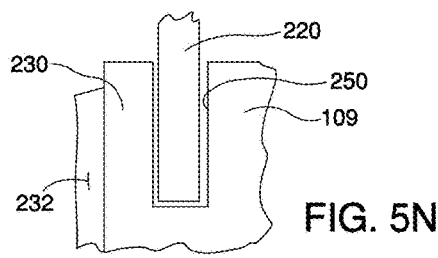
FIG. 5N is a detailed view of portion 5N of FIG. 5L.
Figure 5M:
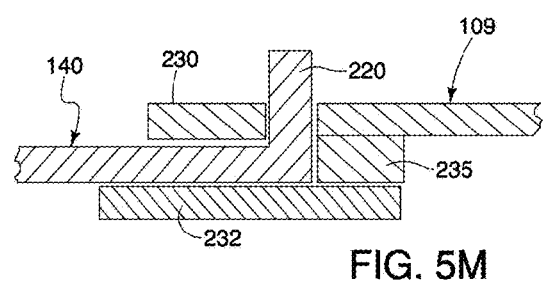
FIG. 5M is a cross-sectional view taken along line 5M-5M of FIG. 5L.
Figure 5O:
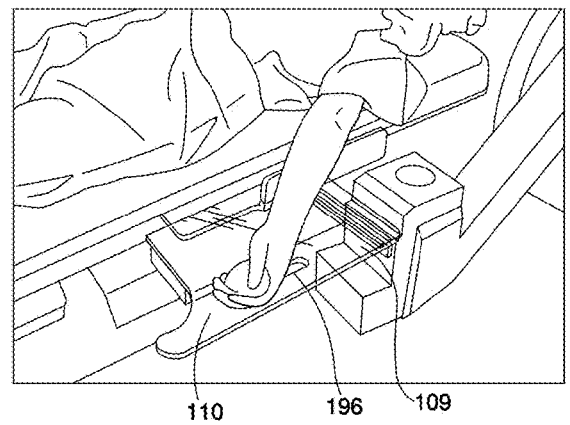
FIG. 5O is an illustration of a patient's arm supported on the arm support platform in a forward position.

As shown in FIG. 5L the support structure 106 is connected in a forward lengthwise horizontal orientation via the elongate slot 250 extending from the backend 190 of the support structure 106. To connect the support structure 106 in a forward horizontal position alongside the base board 140, a thickness of the base board 140 forward of rail 220 is inserted into the gap 234 between attachment rails 230, 232 as shown in FIGS. 5M-5N and the structure 106 is slid along the board 140 to insert the rail 220 on base board 140 into the slot 250 as shown in FIGS. 5L and 5N. As described, movement of the support structure 106 is restricted via base board 140 and rails 230, 232 and lateral movement is restricted via interface of rail 220 and flat portion 109 at slot 250. FIG. 5O illustrate a patient's arm supported on the support structure 106 in the lengthwise orientation for treatment.

The support and base structures 106, 108 described are formed of a rigid material which in illustrated embodiments is a clear transparent rigid material. Illustrative rigid materials include an acrylic material, polycarbonate, plastic, a radiolucent acrylic material, polycarbonate or other radiolucent material, however application is not limited to a particular material and other rigid medical grade materials can be used as will be appreciated by those skilled in the art.

Embodiments of the present application have use for a transradial access procedure for diagnosing and treating heart diseases or other maladies. In a transradial access approach, a catheter is introduced via a radial artery through a patent's wrist. While a physician may introduce the catheter via either the right or left radial artery, often times the procedure is performed on the left radial artery so that the physician can work on the right or opposite side of the patient for the procedure. For left side access, the support structure 106 of the present application is oriented to form a left sideboard and the cushion 104 is orientated so that the cushion side wall is on a left side of the base board 140 and patient. Alternatively, the support structure 106 is orientated to provide a right sideboard and the cushion 104 is orientated so that the cushion side wall on the right side of the patient. In embodiments described, for catheter insertion, the support structure 106 is connected in horizontal position or orientation for radial insertion of a catheter device into the patient's wrist. Once the catheter is inserted, the support structure 106 is shifted to the upright position to hold the patient's arm in a bent position across the patient's body as described.

Figure 6:
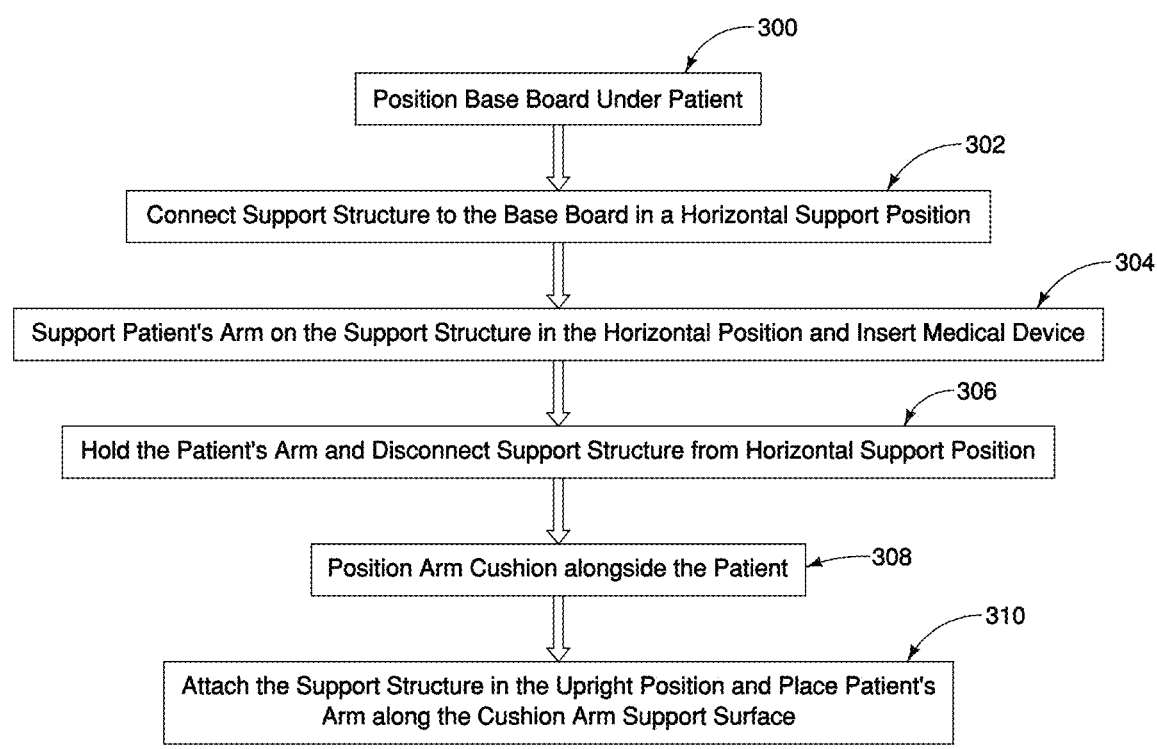
FIG. 6 is a flow chart illustrating steps for support a patient's arm in a first position to insert a catheter and a second position for treatment.

FIG. 6 is a flow chart illustrating steps of an illustrated embodiment using the assembly of the present application for a medical procedure requiring insertion of a catheter into a patient. As shown in step 300, the base board 140 is slid under the patient, and the support structure 106 is attached to the base board 140 in a horizontal support position to provide a horizontal arm support platform in step 302. The horizontal support position of the support structure 106 can be orientated in an outward direction alongside the patient as described in illustrated embodiments. In step 304, the patient's arm is supported on an upper surface of the arm support platform and a catheter is inserted into the patient's wrist. Once the catheter is inserted, the patient's arm is lifted and the support structure 106 is detached from the horizontal position in step 306. Thereafter in step 308, the cushion is placed alongside the patient. In step 310, the support structure 106 is attached in the upright position and the patient's arm is bent so that an upper arm of the patient is supported along the cushion arm support surface 152 and the forearm extends laterally across the patient's abdomen. Once the catheter is in place and the upper arm is supported on cushion, the physician has access to the catheterized arm from the opposite side of the patient. For example, if the catheter is inserted into the left arm or wrist, the physician can access the catheter via the right side of the patient.

FIGS. 7A-7C illustrate an alternate embodiment of a support assembly including a support structure 106A connectable to a base structure 108A in different orientations for different applications. As shown in FIGS. 7A-7B, the support structure 106A includes a flat portion 109 having a front arm extension 110 as previously described in other embodiments. An elongate length of the support structure 106A extends from a backend 190 of the flat portion 109 along a curved body length to a front end 192 as shown in FIG. 7A-7B. As previously described, the curved body length forms the angled front arm extension 110 coupled to the flat portion 109. The flat portion 109 has an height extending from a bottom edge to a top edge. As shown, a bottom surface 139 of the front arm extension 110 is spaced from the bottom edge of the flat portion 109 to provide clearance for a patient's body as previously described.

The base structure 108A shown includes a base board 140 having an elongate length between a backend 142 and front end 144 and a width between the inner and outer sides 146, 148 as shown in FIG. 7C. As shown, the base board 140 includes spaced guide rails 400, 402 along the outer side edge 148 of the base board 140 to form an attachment feature to connect the support structure 106A to the base board 140. Guide rails 400, 402 are spaced to form gap 404 or groove (of a tongue and groove connection) between the guide rails 400, 402. Guide rails 400, 402 are connected to the base board 140 and have a length that extends between the backend 142 and front end 144 of the base board 140. In particular, in an illustrated embodiment (not shown) guide rails 400, 402 are glued to the base board 140 via elongate grooves extending between the backend 142 and front end 144 along the outer edge 148 of the base board 140. Edge blocks 406, 408 extend alongside rails 400, 402 to provide rigidity and support. Similar to previous embodiments, the base board 140 includes tapered front and back edges and a tapered inner edge 146 spaced from rails 400, 402 for placement of the base board under the patient and/or mattress.

Figure 7D:
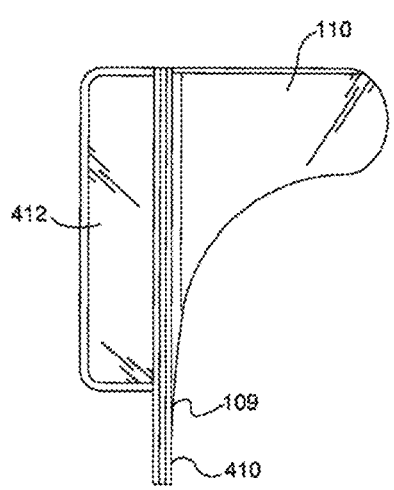
FIG. 7D is a backend view of the support structure illustrated in FIG. 7A.
Figure 7E:
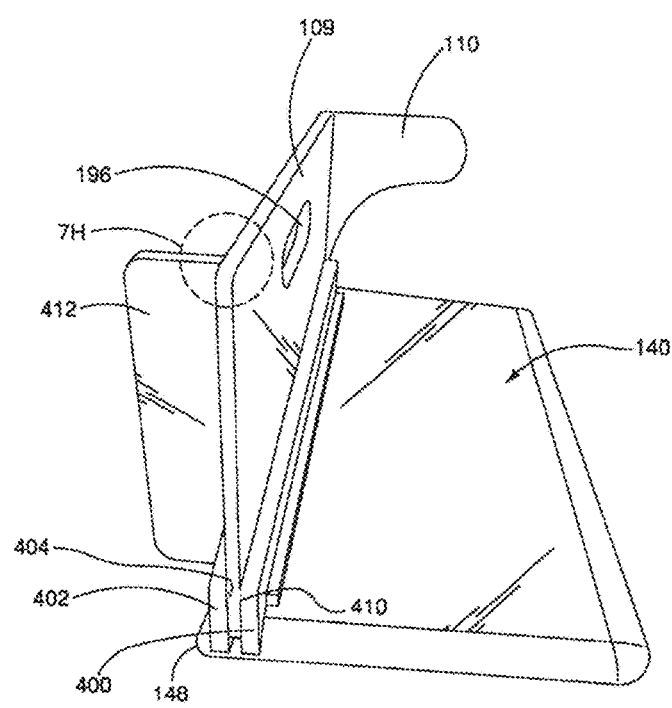
FIG. 7E illustrates the support structure attached to a base board in an upright position or orientation.
Figure 7F:
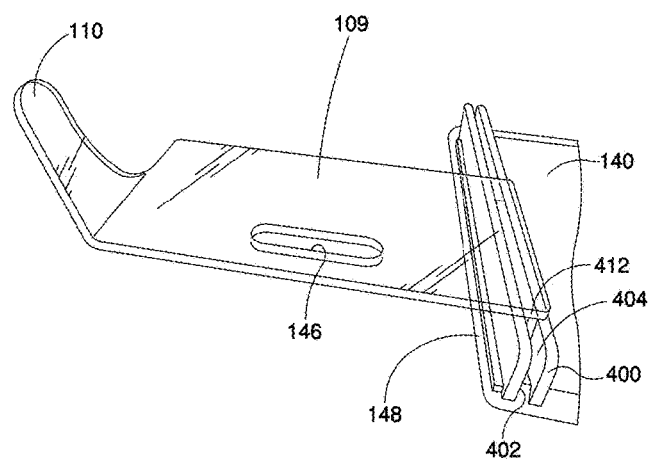
FIG. 7F illustrates the support structure attached in a horizontal orientation.

As shown in FIGS. 7A and 7D, the flat portion 109 of the support structure 106 includes an upright attachment rail 410 along a bottom edge of the sideboard and an crosswise attachment rail 412 along a back end of the flat portion 109. As shown in FIG. 7D, the upright attachment rail 410 is formed of a bottom portion of the flat portion 109 and has a rail thickness corresponding to the thickness of the support structure 106 or flat portion 109. The gap 404 between rails 400, 402 is sized to interface with attachment rail 410 to retain the flat portion 109 and structure in the upright orientation for use as shown in FIG. 7E. The crosswise attachment rail 412 extends generally perpendicular to an outer surface of the flat portion 109 as shown in FIGS. 7D-7E. Crosswise attachment rail 412 is inserted between guide rails 400, 402 of base board 140 to retain the support structure 106 in a horizontal orientation as shown in FIG. 7F. In particular as shown, the back edge of the flat portion 109 is connected alongside the outer edge 148 of the base board 140 so that the length of the support structure 106 extends outwardly as shown. The support structure or board 109 incudes a cut-out handle 196 to facilitate placement of the flat portion 109 and structure in different orientations as shown in FIGS. 7E-7F.

Figure 7G:
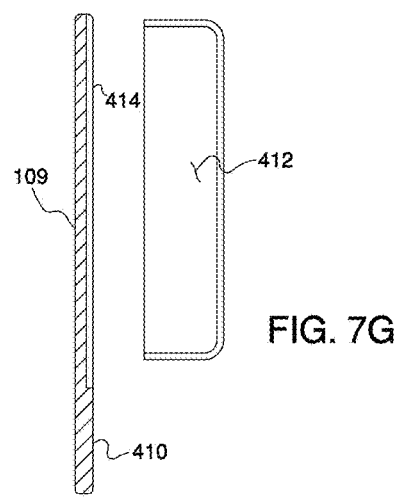
FIG. 7G illustrates a groove in the support structure for attaching a crosswise attachment rail to the support structure.
Figure 7H:
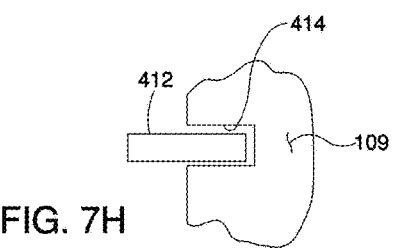
FIG. 7H is detailed top view of portion 7H in FIG. 7E illustrating attachment of the crosswise attachment rail in groove.

FIGS. 7G-7H illustrate attachment of the crosswise attachment rail structure 412 to the support structure 106 via a groove 414 formed along the outer surface of the flat portion 109. The groove 414 has a length corresponding to the length of the attachment rail structure 412. A lower end of the attachment groove 414 is spaced from the bottom edge of the flat portion 109 an offset distance corresponding to the height of attachment rail 410 to provide clearance for forming the attachment rail 410 along the bottom edge of the flat portion 109. The second end of the attachment groove 414 is located proximate to the top edge of the flat portion 109. The length of the crosswise rail 412 is secured within the groove 414 via an adhesive or other attachment means to secure the crosswise rail 412 to the flat portion 109.

Figure 8A:
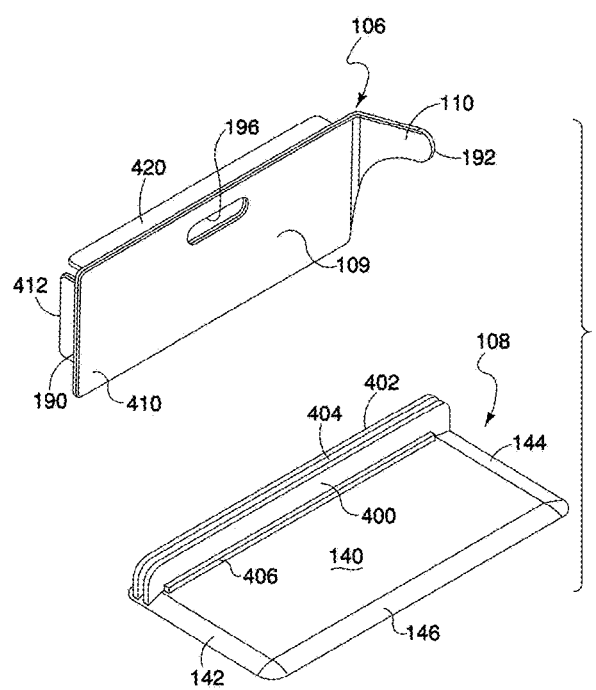
FIG. 8A is an exploded view of an embodiment of a support structure attachable to a base structure.

FIG. 8A illustrates another embodiment of a support structure 106 or board 109 removably attachable to base structure or base board 140 in different orientations for different applications and uses. Similar to the embodiment illustrated in FIGS. 7A-7H, the support structure includes attachment rail 410 to hold the support structure 106 in the upright position and crosswise attachment rail 412 to secured the support structure 106 in the horizontal position to form the support platform. Additionally, in the embodiment shown, the flat portion 109 includes lengthwise attachment rail 420 having a length extending between the back end 190 and the front end 192 of the support structure (or flat portion 109). The lengthwise attachment rail 420 is inserted between guide rails 400, 402 on the base board 140 to support the flat portion 109 in a horizontal orientation where the length of the support structure or board 109 extends alongside the outer edge 148 of the base board as shown FIG. 8B.

Figure 8B:
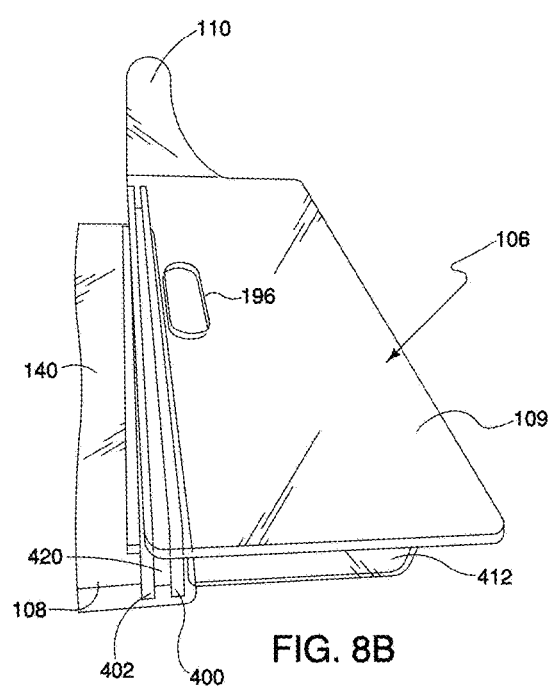
FIG. 8B illustrates the support structure or board connected in a lengthwise horizontal orientation.
Figure 8C:
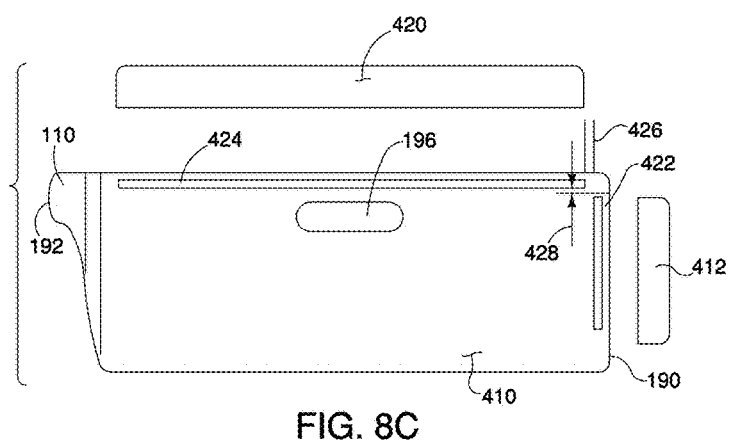
FIG. 8C is an exploded view of a support structure having a crosswise attachment rail and lengthwise attachment rail connected to an outer or lower surface.

As shown in FIG. 8C, the attachment rails 412, 420 are connected to an outer surface of the flat portion 109.

Attachment rail 412 is attached within crosswise groove 422 along the back end of the flat portion 109. Attachment rail 420 is attached within a lengthwise groove 424 along the top edge of the sideboard. As shown in FIG. 8C, a back end of attachment rail 420 is spaced from a front surface of crosswise attachment rail 412 to form a clearance gap 426. The clearance gap 426 has a gap dimension size wider than a width of the guide rails 400, 402 for insertion of the attachment rail 412 between guide rails 400, 402 without interference to position the support structure 106 in the crosswise horizontal orientation. Similarly, attachment rail 420 is spaced from a top edge of attachment rail 412 to form clearance gap 428 for insertion between guide rails 400, 402 for use in the lengthwise horizontal orientation. While in the illustrated embodiment, the support structure is attached to a rectangular base board, embodiments of the sideboard can be attached to other base board 140 designs such as the base board design shown in FIG. 5D.

Figure 8D:
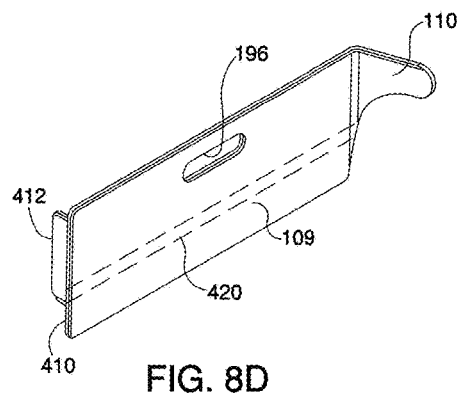
FIG. 8D is an alternate embodiment of a support structure having a crosswise attachment rail and lengthwise attachment rail.

In the illustrated embodiment shown in FIG. 8B, the front arm extension 110 is oriented at the back end when the flat portion 109 is connected to the base board via the lengthwise attachment rail 420. In an illustrated embodiment, front arm extension is rotationally coupled to the flat portion 109 to adjust the orientation of the front arm extension 110 through a plastic hinge or flexible coupling. In an alternate embodiment shown in FIG. 8D, the lengthwise attachment rail 420 can be formed along a bottom portion of the outer surface of the support structure as shown in phantom so that the front arm extension 110 is located forward of the patient when connected in the horizontal orientation to limit interference.

FIG. 9A illustrate an embodiment of a support structure 106 connectable to base board 140 in various orientations for supporting a patient's arm for a medical procedure. As shown, the support structure 106 has a back end 450, a front end 452 and a curved edge surface 456. The flat portion 109 also includes an attachment rail 410 formed by the bottom portion of the board and a lengthwise attachment rail 460 extending from and attached to an outer surface of the support structure 106. The attachment rail 410 and lengthwise attachment rail structure 460 are sized for insertion between guide rails 400, 402 formed along an outer edge of base board 140 as previously described.

Figure 9D:
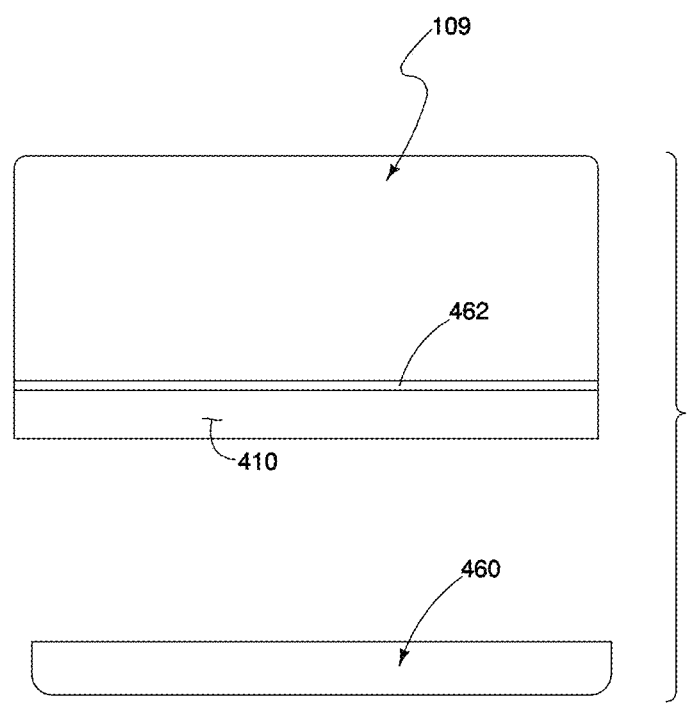
FIG. 9D is an exploded view of the support structure illustrating attachment of a lengthwise attachment rail to the support structure.

The attachment rail 410 is inserted between guide rails 400, 402 to hold the flat portion 109 in the upright position as shown in FIG. 9B to form an upright side board or guard to retain a patient's arm so that the patient's arm does not drop over the sides of a bed or table. The lengthwise attachment rail 460 is inserted between guide rails 400, 402 on the base board 140 to secure the flat portion 109 in the horizontal orientation to support the patient's arm as shown in FIG. 9C. As shown in the horizontal orientation, the curved edge surface 456 forms a perimeter rim to retain and protect the patient's arm on the flat portion 109. As shown in FIG. 9D, the lengthwise attachment rail 460 is connected to an outer surface of the support structure 106 via groove 462. As previously described the groove 462 and attachment rail 460 are spaced from a bottom edge of the sideboard to provide clearance for the attachment rail 410 formed by the bottom edge of the flat portion 109.

Figures 10A, 10B:
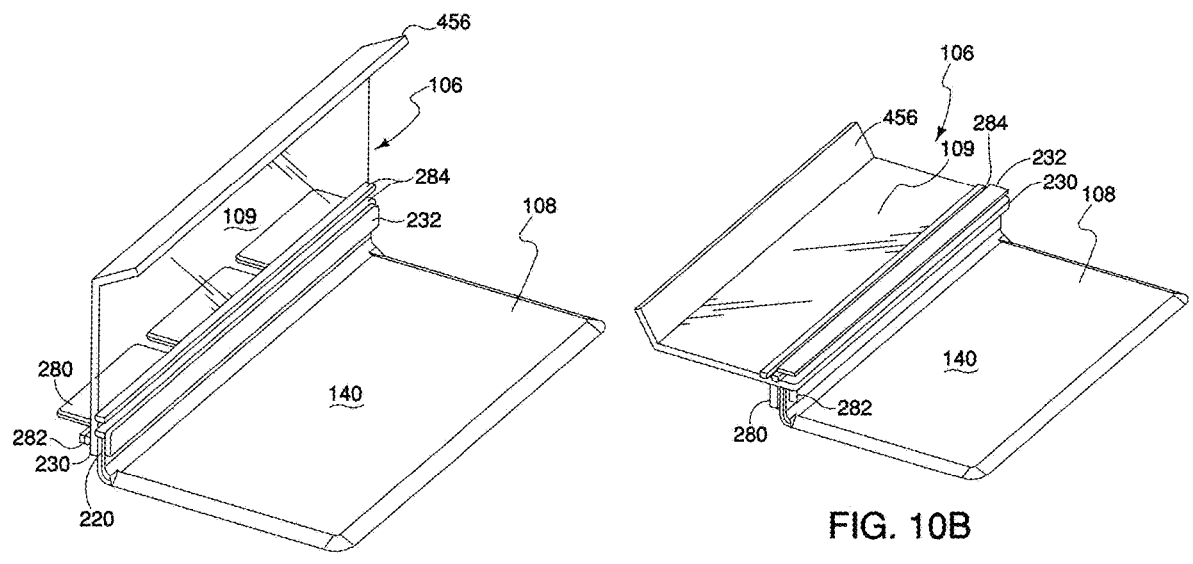
FIGS. 10A-10B illustrate another embodiment showing the support structure connected to a base board in an upright orientation and a horizontal orientation.
Figure 10C:
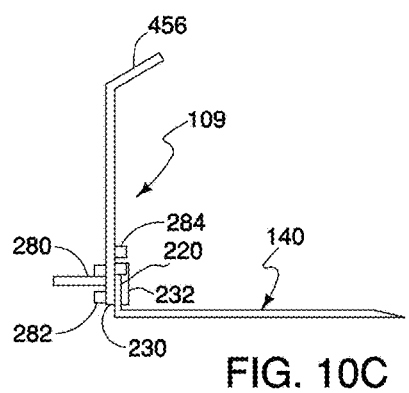
FIG. 10C-10D illustrate the embodiment shown in FIGS. 10A-10B of the support structure connected to a base board in an upright orientation and in a horizontal position or orientation.
Figure 10D:
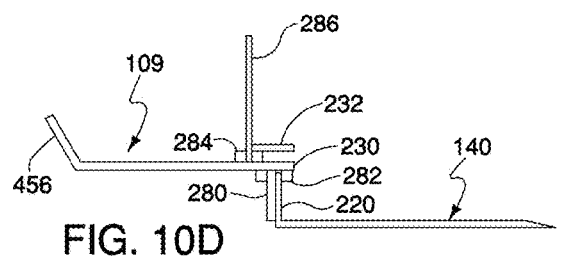

FIGS. 10A-10D illustrate an alternate embodiment of the support structure 106 or attachment connectable to base board 140 in various orientations as previously described. In the illustrated embodiment the base board 140 includes the elongate base rail 220 and the support structure 106 includes attachment rails 230, 232 to connect the support structure 106 to the base board 140 in the upright position as shown in FIGS. 10A and 10C. The support structure 106 also includes lengthwise rails 280, 282 shown in FIGS. 10B and 10D extending from an outer surface of the support structure along a bottom edge portion to connect the support structure 106 in a horizontal orientation as shown in FIGS. 10B and 10D. In the embodiment shown, an inner surface of the support structure includes an elongate block 284 spaced from rail 232 to form an inset slot along a length of the support structure to support a shield 286 as shown in FIG. 10D.

Figure 11A:
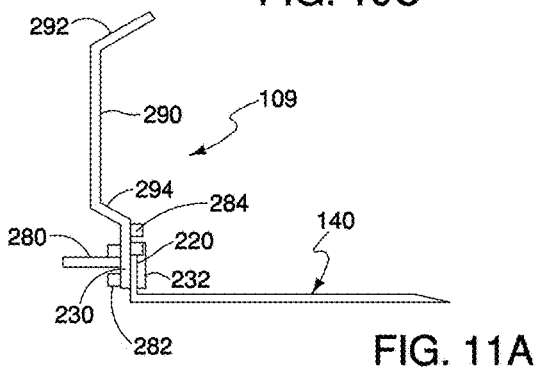
FIGS. 11A-11B illustrate another embodiment of the support structure connected to a base structure or baseboard in the upright position in FIG. 11A and horizontal position shown in FIG. 11B.
Figure 11B:
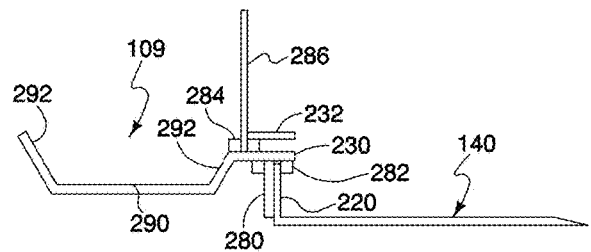
Figure 12A:
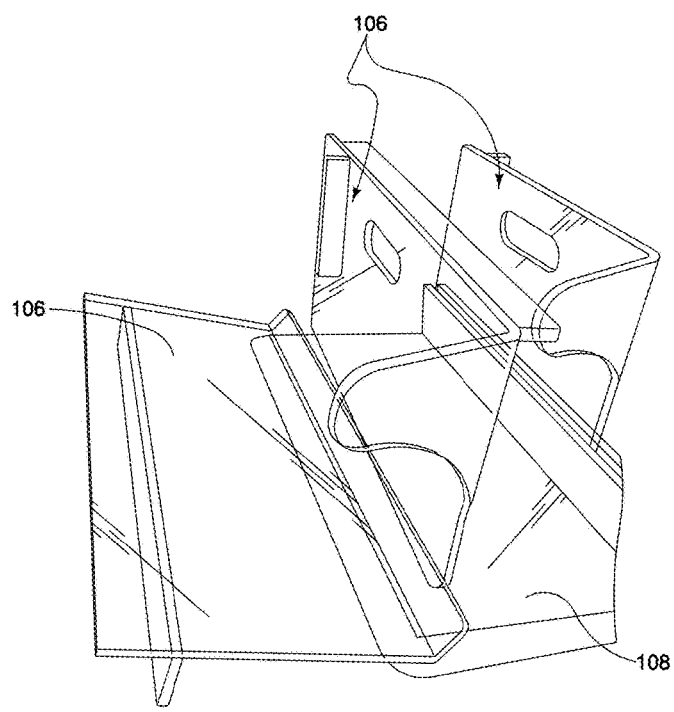
FIG. 12A illustrates various support structures or designs attachable to a base board.

FIGS. 11A-11B illustrate an alternate design wherein the shape of the support structure 106 is contoured to form a recessed center portion 290 and raised side edges 292, 294 in the horizontal position as shown in FIG. 11B. A patient's arm is supported along the recessed center portion 290 while the raised side edges 292, 294 protect the patient's arm during a medical procedure. The embodiments illustrated in FIGS. 9A-11B are useful for right arm sideboards or support structures. Left arm sideboards or support structures generally have or require a longer length dimension between the back and front ends to position the back end proximate to the patient's upper arm while the right sideboard embodiments have a shorter length dimension to limit obstructing access to the patient's head area. However application of the present invention is not limited to a particular length. FIG. 12A illustrates embodiments of right and left arm sideboards or support structures for use with a universal base board 140 as shown.

Figure 12B:
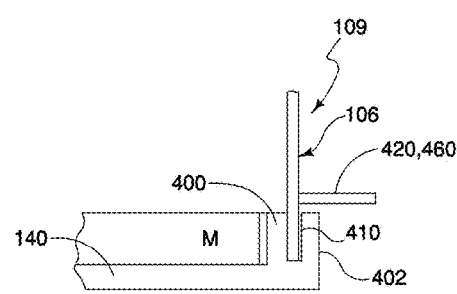
FIG. 12B is a detailed illustration of a base board in use under a mattress with a support structure connected in the upright orientation.
Figure 12C:
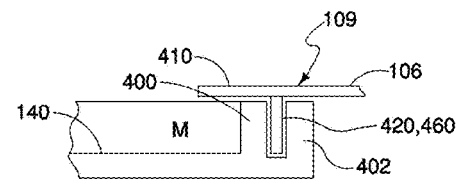
FIG. 12C is the detailed illustration of FIG. 12B with the support structure in the horizontal position.

As shown in FIGS. 12B-12C, the base board 140 is sized to slide under mattress M. As shown the rails 400, 402 and rail 220 (not shown) have an elevated height corresponding to the height of the mattress so that the rails are not elevated above an upper surface of the mattress M. The height elevation of the rails 400, 402 relative to the mattress limits interfere with the patient getting on and off the bed. Illustratively the height of the mattress and guide rails 400, 402 or rail 220 on base board 140 are two (2) inches in height. As illustrated in FIG. 12B, the attachment rails 410, 412 on the support structure 106 have a height corresponding to the height of the base rails to hold the support structure 106 in place for use. Thus, as described, the base board 140 is set in place under mattress M for use prior to the patient getting on the bed. Thereafter the support structure 106 is set in place as described for use. While illustrated embodiments show attachment rails other attachment structures or features may be used to connect the support structure to the base board as will be appreciated by those skilled in the art.

As previously described, the sideboard and base board of illustrative embodiments of the present application are formed of an acrylic material, polycarbonate, plastic, a radiolucent acrylic material, polycarbonate or other radiolucent material for use in a radiation or x-ray zone. The shield 286 as illustrated in FIGS. 10D and 11B is formed of a lead or other shielding material as will be appreciated by those skilled in the art. Embodiments of the present invention provide base board configurations for use as a right or left board or support or right/left board or support depending upon the desired applications. In other embodiments, the base board has a wider front dimension relative to the back dimension and has application for either a left arm sideboard or right arm sideboard. In an alternate embodiment, the base board includes a rail or guide rails along both sides to connect multiple support structures to the base board along opposed sides of the base board 140.

Figure 13A:
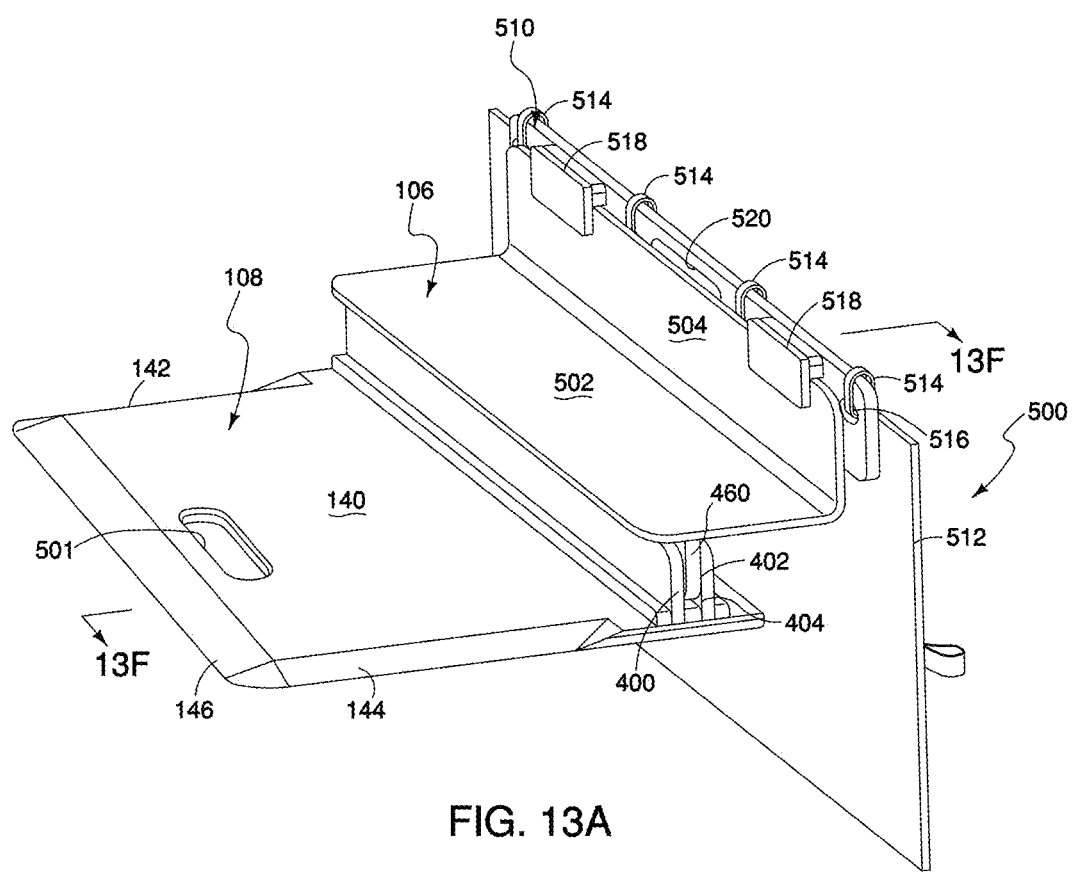
FIG. 13A is a perspective illustration of an assembly of the present application as viewed from a forward end.
Figure 13B:
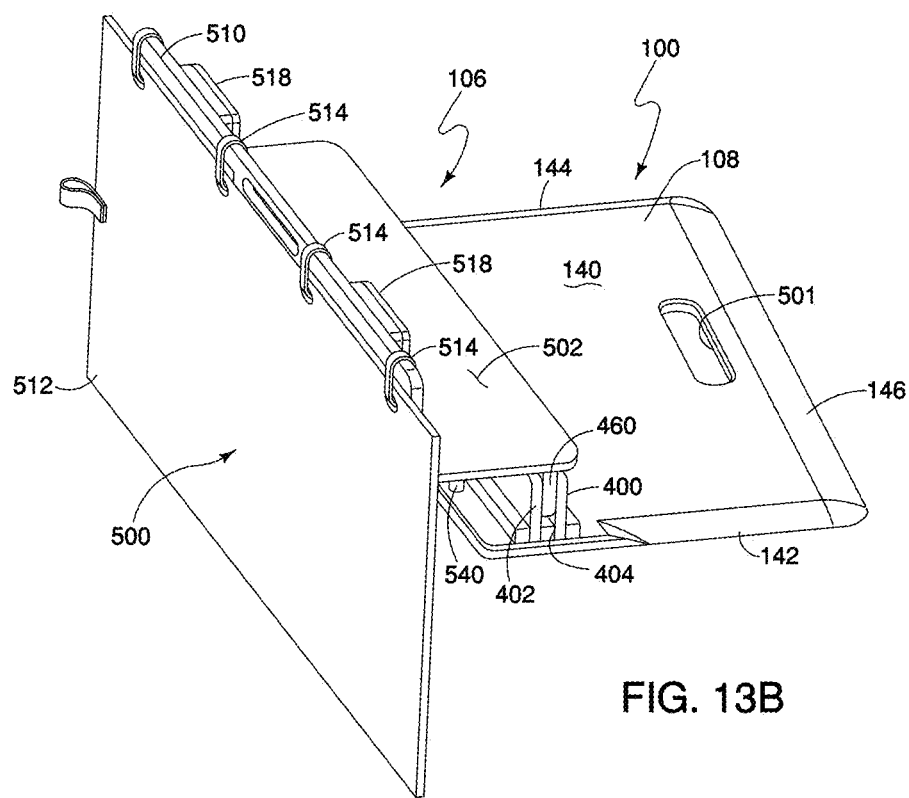
FIG. 13B is another perspective illustration of the assembly of FIG. 13A as viewed from a back end.

FIGS. 13A-13B illustrate another embodiment of a support assembly 100 including a radiation shield 500. As shown, the support assembly 100 includes support structure 106 removably connectable to base structure 108 as previously described. In the illustrated embodiment, the shield 500 is removably coupled to the support structure 106 to shield radiation during a diagnostic or treatment procedure. As shown in FIGS. 13A-13B the base structure 108 is formed of a base board 140 having a generally rectangular shape body having a back end 142, forward end 144 and inner and outer sides 146, 148. As shown, back, forward and side edges 142, 144, 146 of the base board 140 are tapered for placement of the base structure 108 under the patient. In the embodiment shown, the base board 140 has a "cut-out" handle 501 for use to move and position the base board 140.

In the embodiment shown, the support structure 106 is formed of a generally "L" shaped body having a flat portion 502 forming a support surface for the patient's arm and a raised wall 504 along an outer edge of the support structure 106 to retain the patient's arm in place on the flat portion 502 during a medical procedure. In the illustrated embodiment, the support structure 106 is removably connected to the base board 140 through attachment features. In the embodiment shown in FIGS. 13A-13B, the base board 140 includes opposed spaced rails 400, 402 extending between back and forward ends 142, 144 of the base board 140 to form the attachment feature or groove 404 on the base structure and the "L" shaped body includes an attachment rail 460 extending from an underside of the flat portion 502 to form the attachment feature or tongue on the support structure to removably connect the support structure 106 to the base structure 108 or board 140. It should be understood that, application is not limited to the tongue and groove connection described and in alternate embodiments as previously described, rails 400, 402 are formed on the support structure 106 and rail 460 is formed on base board 140.

Figure 13C:
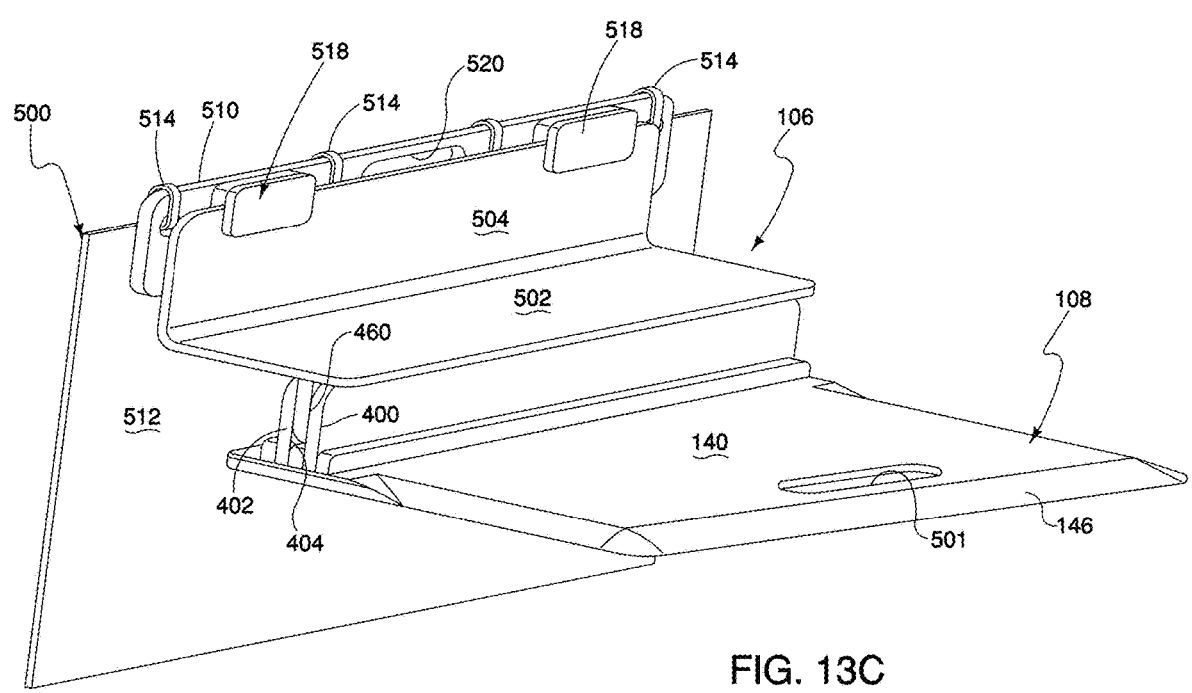
FIG. 13C is another perspective illustration of the assembly shown FIGS. 13A-13B.
Figure 13D:
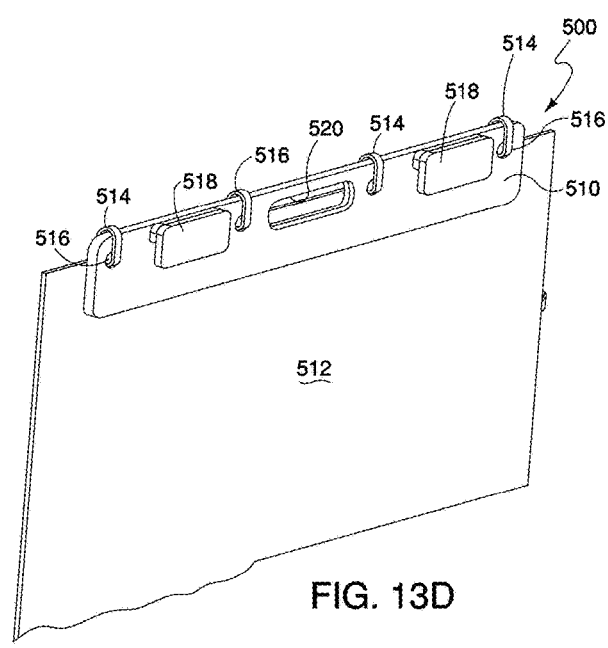
FIG. 13D is a perspective illustration of a shield of the assembly having a headboard folded for attachment to a support structure.
Figure 13E:
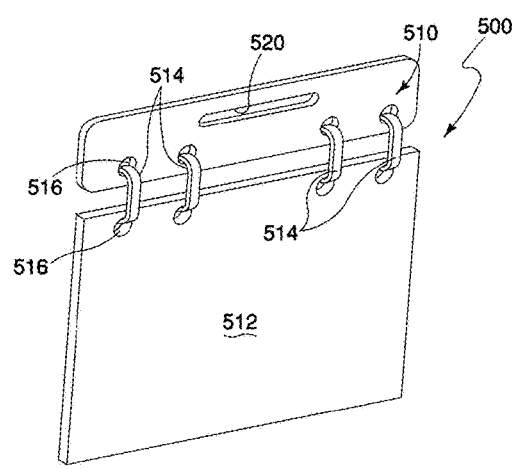
FIG. 13E illustrates the shield of FIG. 13D with the headboard extended.

As shown in FIG. 13A-13C, shield 500 is removably connected to the support structure 106 for use. In the illustrated embodiment, the shield 500 includes a headboard 510 and shield curtain 512 connected to the headboard 510. The shield curtain 512 is formed of a radiation blocking material. Illustratively, the curtain 512 is formed of a flexible material enclosing a radiation blocking structure or body formed of a lead or tungsten material or other radiation blocking material. As shown, the curtain 512 is coupled to the headboard 510 through a plurality of attachment rings 514 to allow the curtain 512 to move or rotate relative to the headboard 510. As shown in FIGS. 13D-13E, the attachment rings 514 have a diameter size to extend through openings 516 on the headboard 510 and curtain 512 to rotationally connect the headboard 510 to the curtain 512. As shown, the elongate headboard 510 includes a plurality of spaced attachment clips 518 to removably connect the shield to the raised side wall 504 of the support structure 106 for use. As shown, the headboard 510 includes a handle opening 520 or cut-out to transport the shield 500 prior to and following use. Although a plurality of attachment clips 518 are shown in the illustrated embodiment, alternate embodiments can use a single elongate attachment clip or other similar device.

Figure 13F:
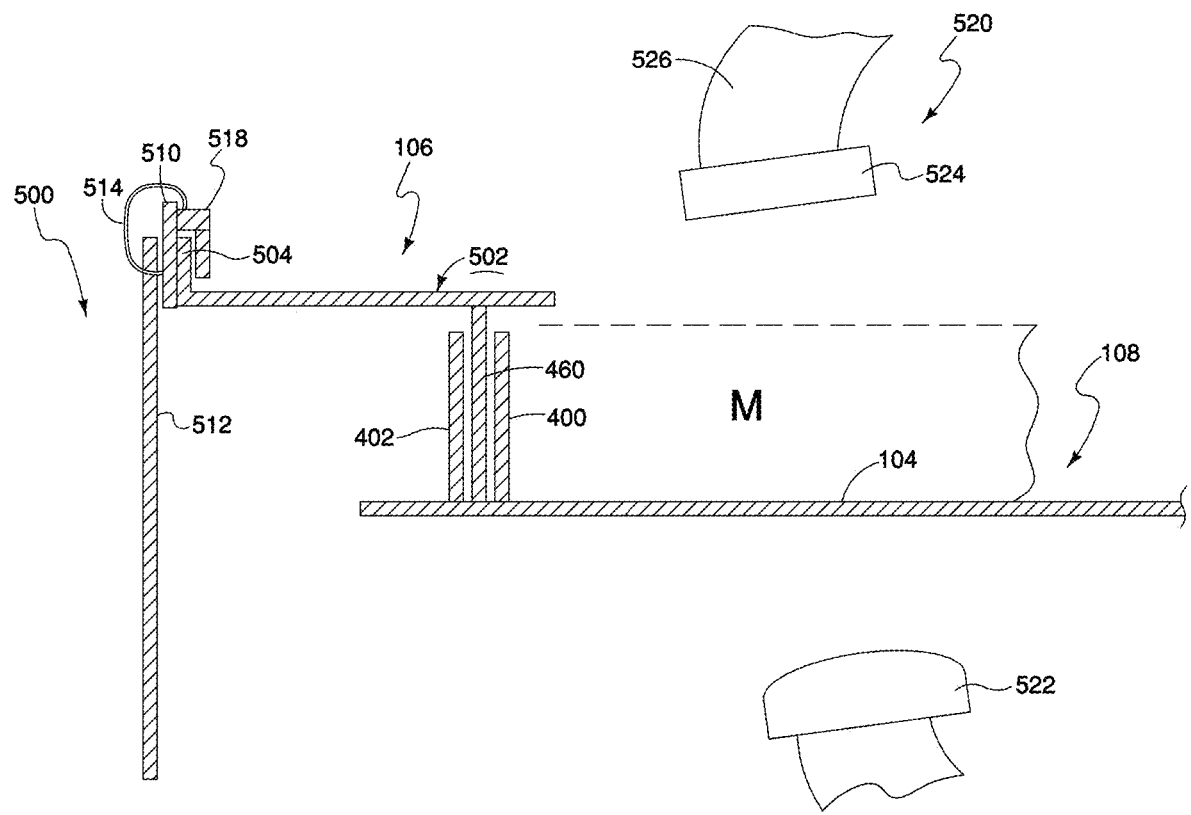
FIG. 13F is a cross-sectional view as taken generally along line 13F-13F of FIG. 13A illustrating the shield attached to the arm support structure to shield radiation from an imaging device.

For use the base board 140 is slid under the patient or mattress M shown in phantom in FIG. 13F on a surgical table so that the flat portion 502 of the support platform 106 is alongside the patient as previously described. As schematically shown, a height of the rails 400, 402 is sized to provide clearance for the mattress M when the support structure 106 is connected to the base board through the tongue and groove attachment or connection. The support structure 106 is used to support a patient's arm during a transradial catherization or other procedure to access a patient's wrist for treatment. During the catherization procedure, an imaging device, such as an x-ray imaging device is used to assist navigation and treatment. The imaging device as schematically shown includes an imaging head 520 having an emitter device 522, such as an x-ray tube and detector device 524 for imaging. As schematically shown, the emitter and receiver devices 522, 524 are coupled to a "C" shaped arm 526 (partially shown) which is adjustable to adjust the orientation of the imaging head for imaging.

In the embodiment shown in FIG. 13F, the emitter device 522 of the imaging head is orientated below the support structure 106 and base board 140. In the illustrated embodiment, the base board 140 and support structure 106 are formed of a clear transparent or radiation translucent material such as acrylic, polycarbonate, or other radiolucent material so that x-rays from an imaging head 520 (emitter device 522) on the underside can pass through the base board 140 and support structure 106. As shown, during the procedure the headboard 510 is rotated so that the headboard 510 and curtain 512 overlap and clips to the raised side wall 504 of the support structure 106 to secure the shield 500 for use. As shown, the length of the curtain 512 is sized to block radiation to limit the radiation field to protect medical personnel from exposure. In an illustrative embodiment, a length of the curtain 512 (shield) is 30 inches. During the procedure, the orientation and position of the imaging head 520 is adjusted to capture the desired image. The width dimension of the platform and raised side wall 504 of the "L" shaped body are sized to provide sufficient clearance for rotation of the "C" arm 526 to adjust the orientation of the imaging head 520 (emitter and receiver devices 522, 524).

Figure 14A:
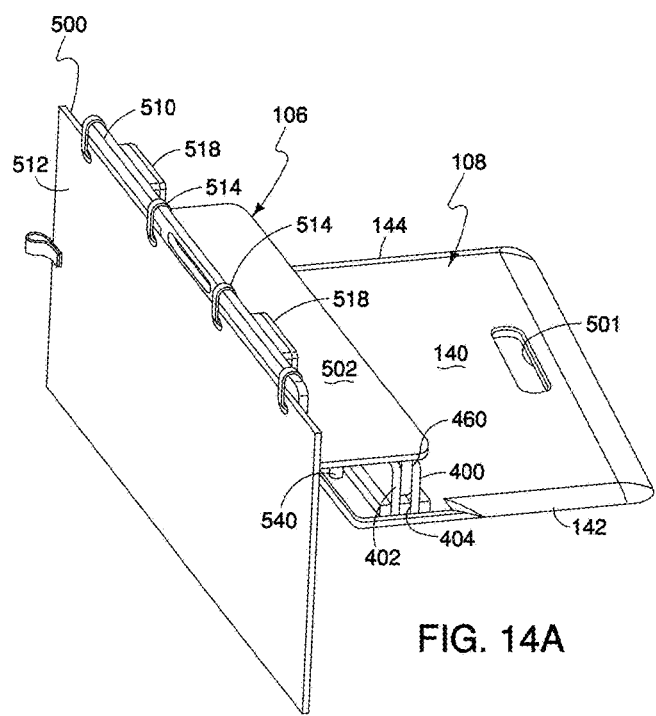
FIG. 14A illustrates another embodiment of the apparatus and shield of the present application.
Figure 14B:
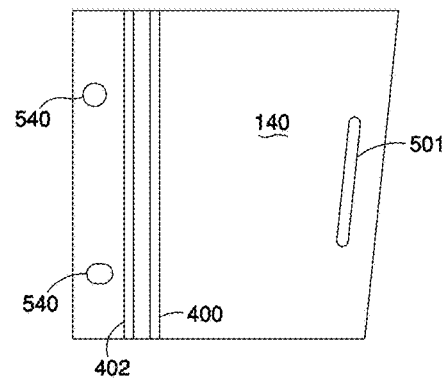
FIG. 14B is a top view of a base board of the apparatus illustrated in FIG. 14A.
Figure 14C:
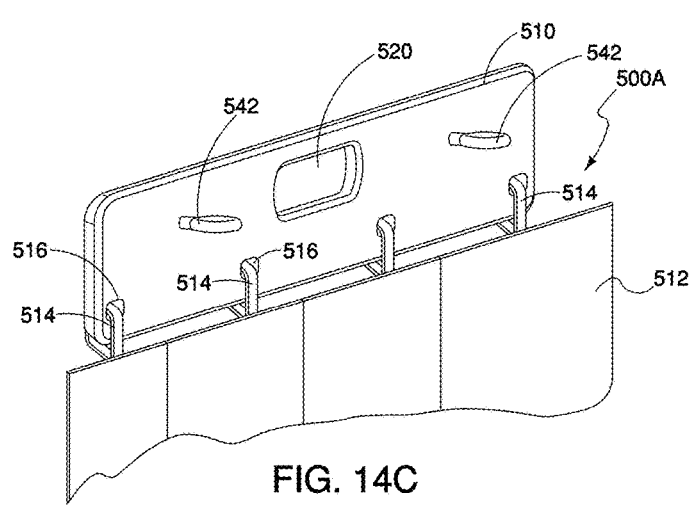
FIGS. 14C-14D are front and back side views, respectively, of a shield removably connectable to the base board of the assembly.
Figure 14D:
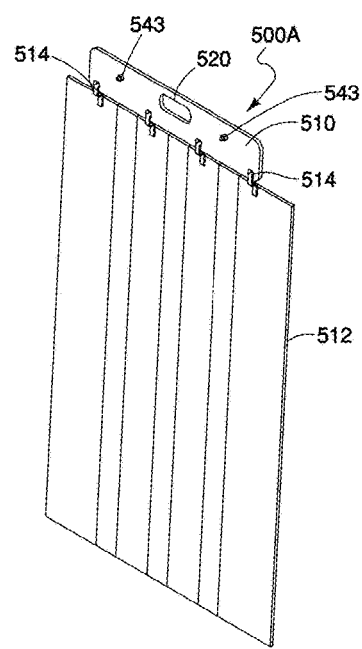
Figure 14E:
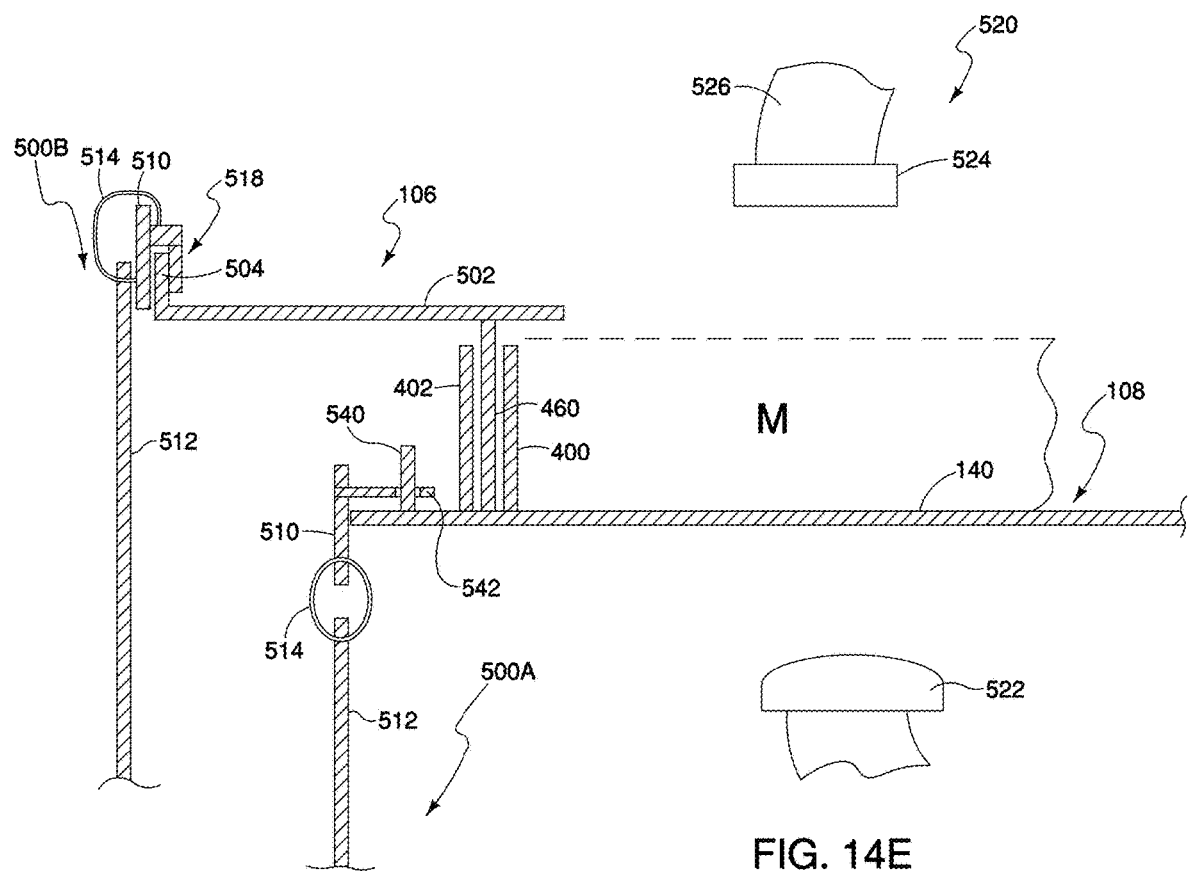
FIG. 14E is a cross-sectional view illustrating connection of shields to the base board and arm support structure of FIG. 14A-14B.

FIGS. 14A-14B illustrate another embodiment of an assembly of the present application where like numbers are used to refer to like parts in the previous FIGS. As shown, in FIGS. 14A-14B, the base board 140 includes a plurality of pegs 540 extending from an upper side of base board 140 between outer side edge and rails 400, 402 of the tongue and groove connection to removably connect shield 500A shown in FIGS. 14C-14D to base board 140. As shown, shield 500A includes a plurality of hook rings 542 attached to the headboard 150 via fasteners 543 shown in FIG. 14D. The hook rings 542 have a diameter opening sized to fit over pegs 540 to removable connect the shield 500A to the base board 140 or structure as shown in FIG. 14E. As shown, shield 500A forms a first shield extending below the base board 140.

In addition to first shield 500A, the illustrative embodiment includes second shield 500B removably connectable to the support structure 106 as previously described. In an illustrated embodiment the length of the first shield 500A extends below the base board 140 and the length of shield 500B has a length to block radiation between the base board 140 and the raised side wall 504 of the support structure 106. Illustratively the length of the first shield 500A is approximately 30 inches long and the length of the second shield 500B is approximately 5 inches long, however, application is not limited to the specific dimensions disclosed.

Figure 15A:
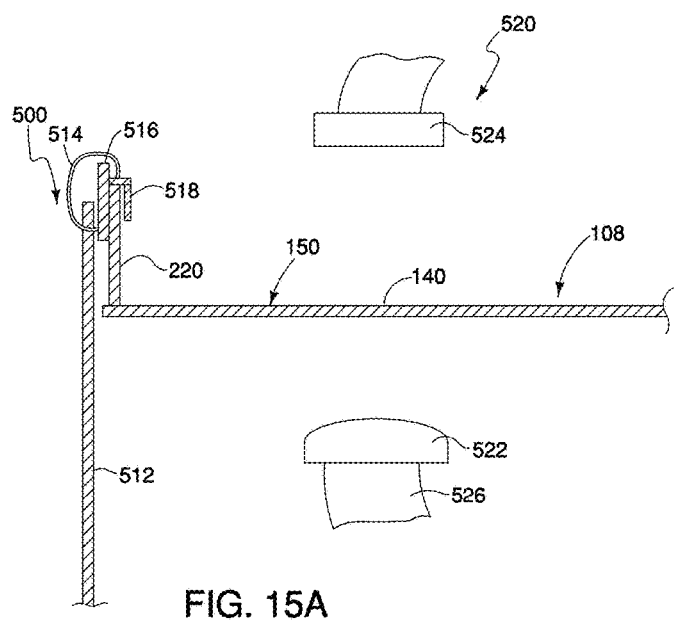
FIG. 15A illustrates another embodiment of the assembly including a base board as shown in FIG. 15B and shield removably connected to the base board for use.
Figure 15B:
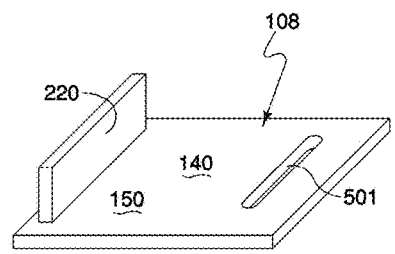

In an alternate embodiment shown in FIGS. 15A-15B the apparatus includes a base board 140 formed of a rectangular shaped body slidably insertable under a patient or surgical table as previously described. The base board 140 is sized so that a portion extends outward from a side edge of the surgical table or mattress M to support a patient's arm. As shown, the base board 140 includes raised edge structure which extends from the upper surface 150 of the base board 140 to retain a patient's arm supported on the upper surface 150 of the base board 140. As shown, the shield 500 is clipped onto rail 220 via clip 518 on base board 140 to protect personnel from radiation as previously described with respect to illustrative embodiments.

Figure 16A:
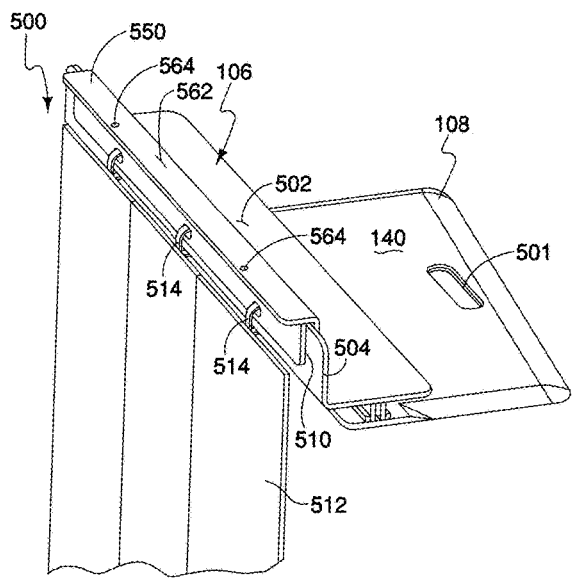
FIGS. 16A-16B are perspective illustrations of an alternate embodiment of the assembly as shown from a front end and back end of the assembly.
Figure 16B:
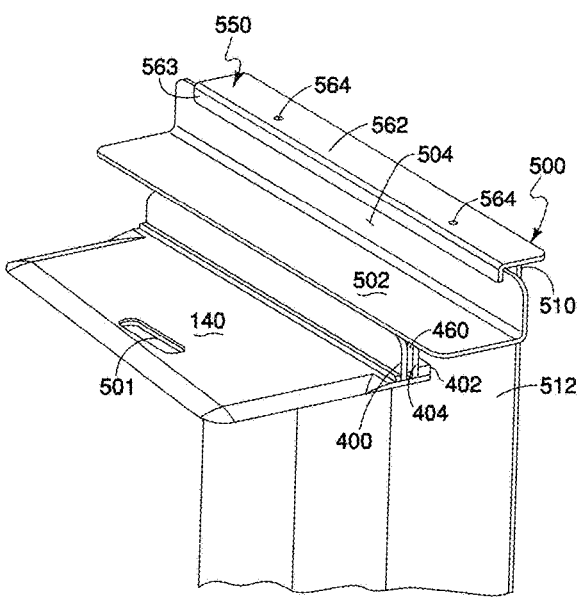
Figure 16C:
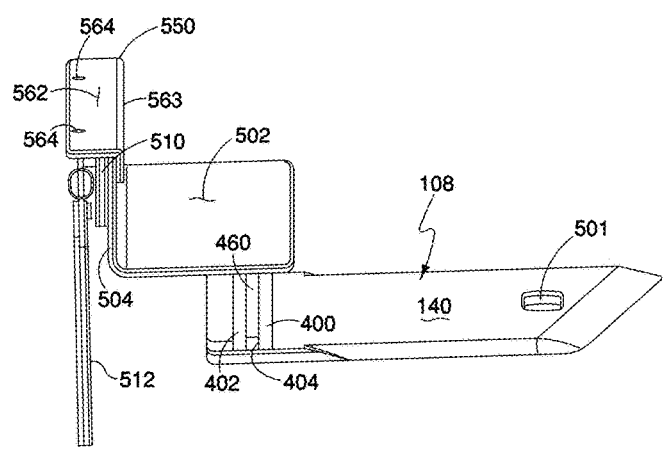
FIG. 16C is a side elevational view of the assembly of FIGS. 16A-16B shown with the shield connected to the arm support structure.

FIGS. 16A-16C illustrate another embodiment of the apparatus where like numbers are used to identify like parts in the previous FIGS. In the illustrated embodiment the curtain 512 of shield 500 is connected to a head structure which includes headboard 510 and an "L shaped structure 550 connected to the headboard 510 to cooperatively form a "U" shaped attachment feature to removably connect the shield 500 to the raised side wall 504 along the support structure connected to the base structure 108 in the horizontal orientation. As shown, the length of the "L" shaped structure 550 extends along the length of the shield 500 to removable connect the shield 500 to the support structure 106.

Figure 16D:
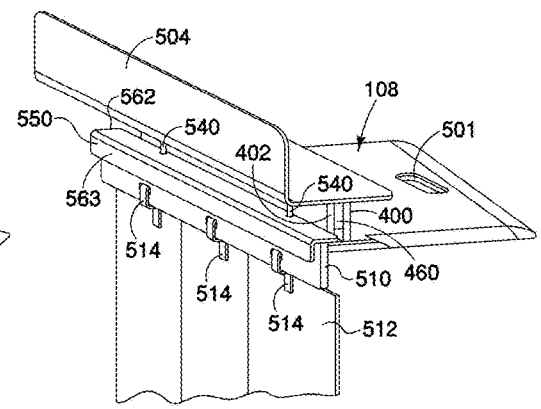
FIGS. 16D-16E illustrate the assembly of FIGS. 16A-16B with the shield connected to the base board.
Figure 16E:
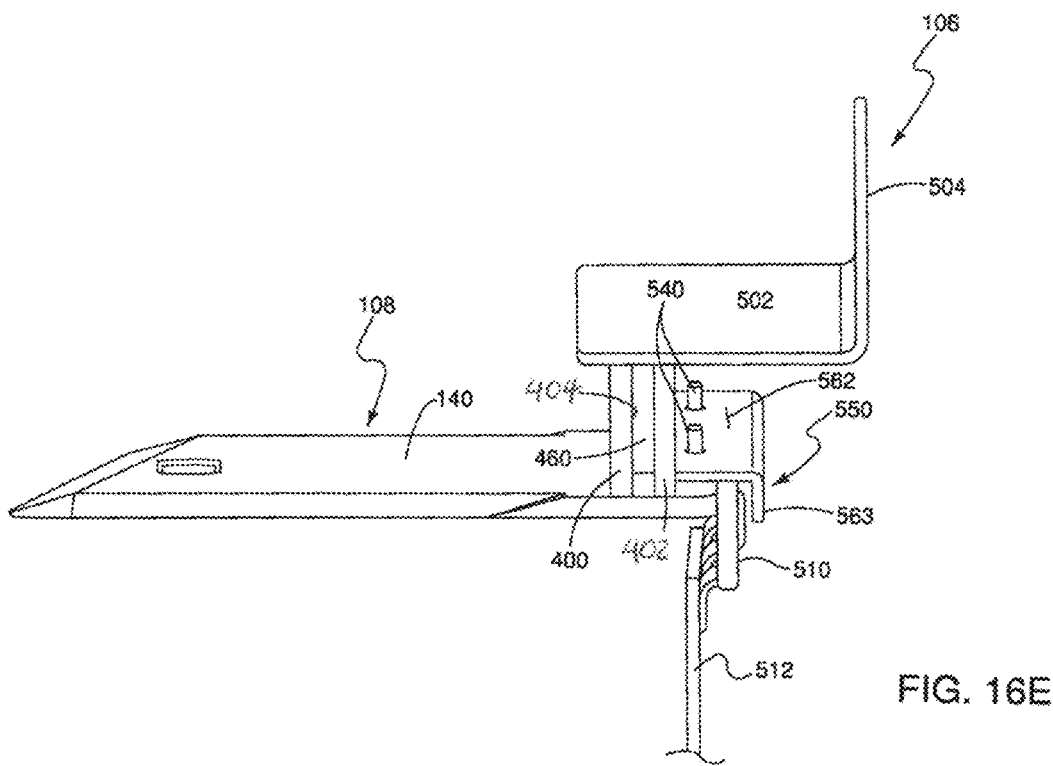
Figure 16F:
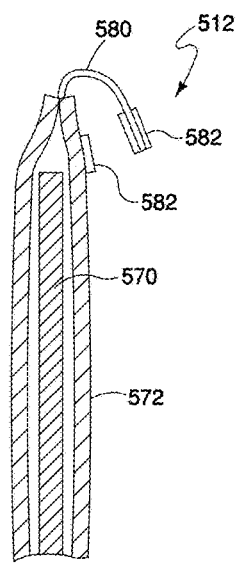
FIG. 16F illustrates an embodiment of the shield curtain in cross-section connectable to the head board through a fastener strap.

The L shaped structure 550 as shown includes a top plate 562 and a side plate 563. Alternatively, as shown in FIGS. 16D-16F, the baseboard 140 of the illustrative embodiment includes upright pegs 540 as previously described with respect to FIGS. 14A-14B. The pegs 540 are sized to extend through attachment openings 564 formed on a top plate 562 of the "L" shaped structure 550 as shown in FIGS. 16A-16B. As shown, the attachment openings 564 are spaced from the headboard 150 and edge side plate 563 so that the top plate 562 rests on an upper surface of the base board 140 and the pegs 540 extend through the attachment openings 564 to removably connect the shield 500 to the base board 140. Thus, in the illustrated embodiment, the shield 500 can be optionally connected to the support structure 106 as shown in FIGS. 16A-16C or the base board 140 as shown in FIGS. 16D-16E.

Figure 16G:
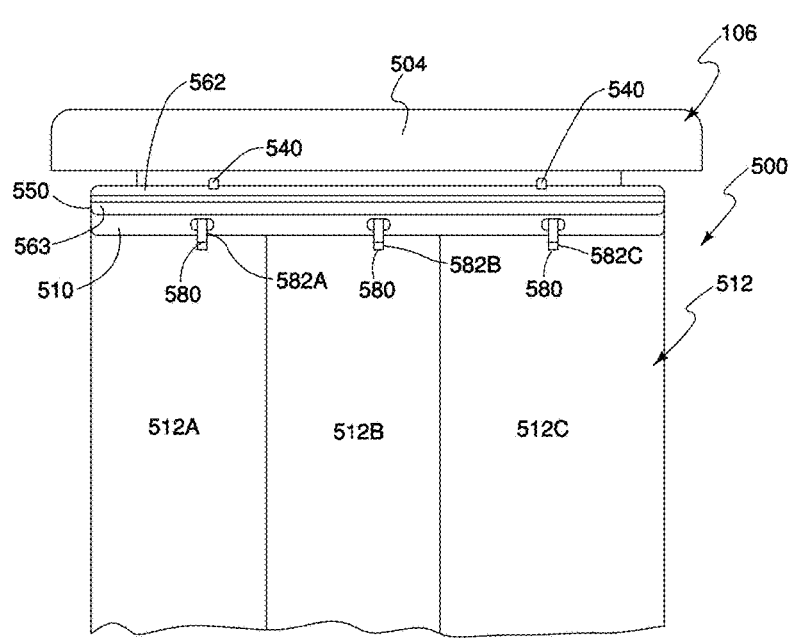
FIG. 16G illustrates an embodiment of the shield including a plurality of curtain sections.

As shown in FIG. 16F, the curtain 512 for the shield 500 is formed of an elongate shield structure 570 enclosed within a flexible outer cover 572 as previously described. In illustrated embodiments, the cover 572 is formed of a nylon or fabric material and the perimeter edges of the nylon or fabric material are connected along a seam to enclose the shield structure 570. The curtain 512 is removable attached to the head structure 510 (not shown) through a fastener strap 580 connected to the curtain or cover. As schematically shown, the strap 580 includes male and female snap elements 582. As shown in FIG. 16G. the fastener strap 580 extends through an opening 516 in the headboard 510 or structure to secure the curtain 512 to the headboard 510 through connection of snap elements 582 As shown in FIG. 16G, the curtain 512 includes a plurality of spaced curtain sections 512A-512C connected to the head structure or headboard 510 through a plurality of fastener snaps 582A-582C to form the curtain. Illustrative curtain sections 512A-512C are available from Burkhart Roentgen International, Inc. of St. Petersburg Florida sold under the name of "Snapanel". The curtain sections 512A-512C are sized to have sufficient length to extend from the base board 140 or arm support structure 110 to the floor of a catheter lab or medical facility.

Figure 17A:
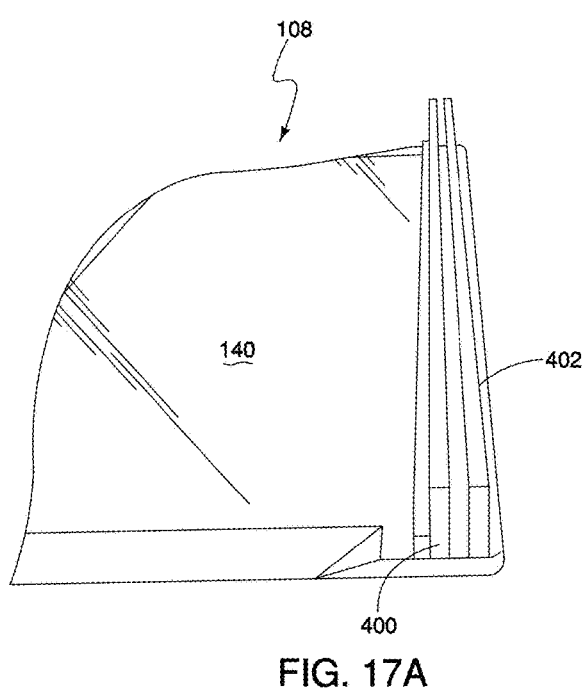
FIG. 17A illustrates an embodiment of the base board of the assembly of the present application.
Figure 17B:
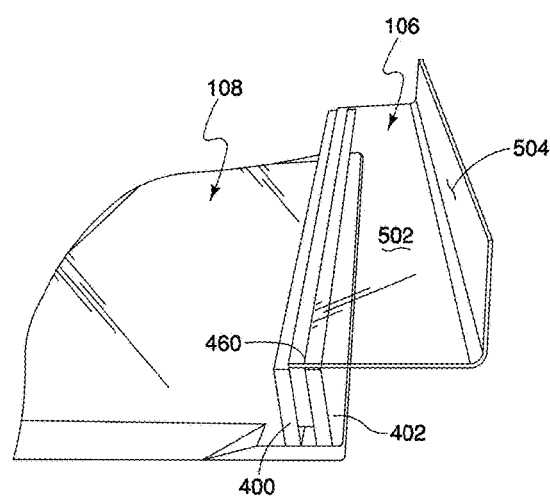
FIG. 17B illustrates the base board with the arm support structure attached.
Figure 17C:
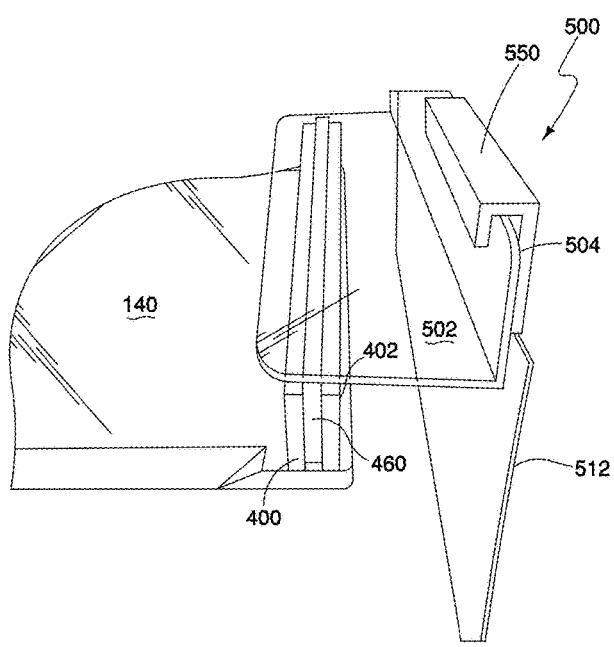
FIG. 17C illustrates the base board with the arm support structure attached and the shield removably attached to the arm support structure.
Figure 17D:
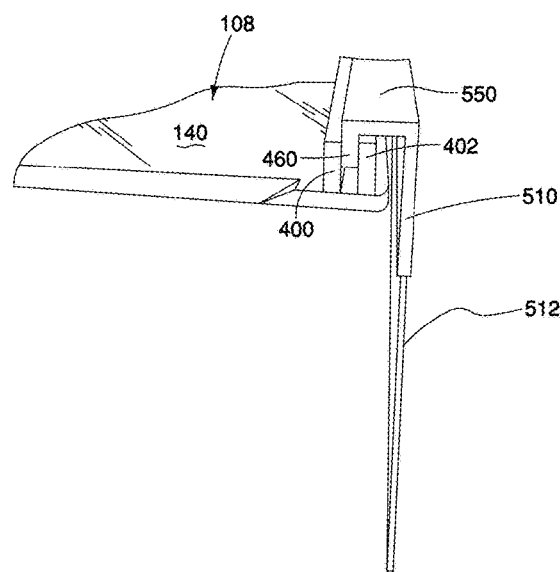
FIG. 17D illustrates the base board with the shield removably attached to the base board.

FIGS. 17A-17D progressively illustrate assembly of the apparatus for use. As progressively shown in FIGS. 17A-17B, the arm support structure 106 is removably connected to the base board 140. Thereafter as shown in FIG. 17C, the shield 500 can be connected to the support structure 106 as previously described in FIGS. 16A-16C or to the base board 140 as shown in FIG. 17D via rails 400, 402 when the support structure 106 is removed as previously described with respect to FIGS. 16D-16E.

Embodiments of the present application have use for a transradial access procedure for diagnosing and treating heart diseases or other maladies. While a physician may introduce the catheter via either the right or left radial artery, oftentimes, the procedure is performed on the left radial artery so that the physician can work on the right or opposite side of the patient for the procedure. For left side access, the base board 140 is inserted on the left side of the patient so that the arm support 106 is along the patient's left side. Alternatively, for right side access the base board 140 is inserted on the right of the patient so the arm support is orientated along the patient's right side. In illustrated embodiment a width of the inner side is tapered to provide a narrow wide proximate to the head of the patent and a wider width proximate to the legs of the patient. As described in illustrative embodiments, the shield is removable attached to the base board 140 or arm support structure 106 to shield radiation from an imaging device.

While illustrative embodiments have been described, application is not limited to the particular embodiments described and changes and modifications can be made as will be appreciated by those skilled in the art. For example, while illustrative embodiments disclose particular attachment features application is not limited to the particular attachment features shown or a particular order of steps. In illustrated embodiments, the support structure or sideboard includes a flat portion and front arm extension integrally formed with the flat portion however application is not limited to an integrally formed construction as described. As will be appreciated by those skilled in the art any of the cushion embodiments can be used with the support frame or structure for left arm radial access or other procedure. While the illustrated base structures includes a base board, application is not limited to the base structure shown. Additionally, while illustrative embodiments disclose a cut-out handle, application is not limited to the cut-out handle shown and other handle constructions may be used.

What is claimed is:

1. An assembly for medical applications comprising:
a base board sized for placement under a patient or mattress having an inner side edge and an outer side edge;
an attachment having an attachment board and a front arm extension angled relative to the attachment board; and
tongue and groove attachment features configured to removably connect the attachment to the outer side edge of the base board in an upright orientation where opposed surfaces of the attachment board form inner and outer surfaces and in a generally horizontal orientation where the opposed surfaces form upper and lower surfaces and wherein a dimension between a top edge and a bottom edge of the front arm extension is sized so that in the upright orientation the bottom edge is elevated above the base board to provide clearance between the front arm extension and the base board for a patient's body and said tongue and groove attachment features including one or more rail structures forming one or more elongate grooves between side walls of spaced rails and one or more tongues sized for insertion into the one or more elongate grooves and the length of the one or more rail structures and grooves extending between an opened front end and an opened back end of the one or more rail structures so that the one or more tongues are slideable along said one or more grooves and through the opened front and back ends of the one or more rail structures to slideably adjust a longitudinal position of the attachment relative to the base board in the upright orientation and the generally horizontal orientation to align the attachment and the front arm extension relative to the patient for treatment.

2. The assembly of claim 1 wherein the attachment board includes an elongate length dimension between opposed cross edges and a width dimension between opposed longitudinal edges and the width dimension is less than the length dimension and the outer side edge of the base board including a first tongue or groove attachment feature and the attachment including a second tongue or groove attachment feature having a width dimension and length dimension larger than the width dimension and the length parallel to at least one of the longitudinal edges of the attachment to connect the one longitudinal edge of the attachment to the base board in the upright orientation and a third tongue or groove attachment feature having a width dimension and a length dimension larger than the width dimension and the length dimension is parallel to at least one of the cross edges of the attachment to attach the one cross edge to the base board in the generally horizontal orientation.

3. The assembly of claim 2 wherein the one or more rail structures forming the one or more grooves is formed on the base board and the one or more tongues including a first tongue formed via a thickness of the attachment board to connect the attachment in the upright orientation and a second tongue is formed of an elongate rail attached to a surface of the attachment board parallel to the one cross edge to connect the attachment in the generally horizontal orientation.

4. The assembly of claim 3 wherein the generally horizontal orientation is a first horizontal orientation and the attachment further comprises a third tongue on the attachment to connect the attachment to the groove on the base board in a second horizontal orientation traverse to the first horizontal orientation.

5. The assembly of claim 1 wherein the one or more rail structures includes one rail structure on the attachment forming a lengthwise groove between the side walls of the spaced rails extending lengthwise along a longitudinal edge of the attachment and the one or more tongues include an elongate rail on the base board to form a first tongue to support the attachment board in the upright orientation and a thickness of the base board along the outer side edge is sized for insertion into the lengthwise groove to form a second tongue on the base board and the attachment including an end slot between opposed sides of a cross width of the attachment wherein the second tongue inserts into the lengthwise groove on the attachment and the elongate rail on the base board extends into the end slot to support the attachment in the generally horizontal orientation.

6. The assembly of claim 5 wherein the generally horizontal orientation is a first horizontal orientation and the lengthwise groove is a first groove and the attachment further comprises a second crosswise groove configured to engage the first tongue on the base board to support the attachment in a second horizontal orientation.

7. The assembly of claim 1 wherein the one or more rail structures includes one rail structure on the base board forming one groove and the one or more tongues include a first tongue on the attachment sized for insertion into the one groove to support the attachment in the upright orientation and a second tongue on the attachment sized for insertion into the one groove to support the attachment in the generally horizontal orientation.

8. The assembly of claim 1 and comprising:
an arm cushion having a cross-width dimension between inner and outer sides and the arm cushion including an arm support structure along the inner side of the arm cushion and a side edge structure along the outer side of the arm cushion configured to abut the attachment board in the upright orientation and the arm cushion including a front edge structure extending along a front end of the arm cushion configured to abut the front arm extension in the upright orientation to retain the cushion in place for use.

9. The assembly of claim 1 wherein the one or more rail structures include a first rail structure on the attachment forming a first groove and a second rail structure on the attachment forming a second groove and the one or more tongues includes one tongue on the base board insertable into the first and second grooves to support the attachment in the upright and generally horizontal orientations and the first groove is orientated to slideably support the attachment in the upright orientation and the second groove is orientated to slideably support the attachment in the generally horizontal orientation.

10. The assembly of claim 1 wherein the base board includes a front edge, a back edge, a thickness dimension between upper and lower surfaces and a width of the base board between the inner and outer side edges is tapered between the front edge and the back edge and the tongue or groove attachment features include one of the one or more rail structures or tongues formed along the outer side edge of the base board.

11. An assembly for medical applications comprising:
a base board having a thickness dimension sized for placement under a patient or mattress; and
an attachment including an attachment board having a width dimension between spaced longitudinal edges and a length dimension between spaced cross edges and the attachment includes first and second tongue or groove attachment features to connect the attachment to a tongue or groove attachment feature on the base board in an upright orientation and a horizontal orientation and the first tongue or groove attachment feature having a width dimension and a length dimension larger than the width dimension and the length dimension is generally parallel to at least one of the longitudinal edges to connect the at least one longitudinal edge of the attachment to the base board in the upright orientation and the second tongue or groove attachment feature having a width dimension and a length dimension larger than the width dimension and the length dimension is orientated generally parallel to an at least one of the spaced cross edges to connect the at least one cross edge of the attachment to the base board in the horizontal orientation.

12. The assembly of claim 11 wherein the tongue or groove attachment feature on the base board is an elongate rail forming a tongue and the attachment includes a first groove along the one longitudinal edge of the attachment and a second groove generally transverse to the first groove along the one cross edge to form the first and second tongue or groove attachment features on the attachment to connect the attachment to the base board in the upright orientation and in the horizontal orientation.

13. The assembly of claim 11 wherein the tongue or groove attachment feature on the base board includes an elongate groove and the first and second tongue or groove attachment features on the attachment comprise first and second rails sized for insertion into the groove on the base board wherein the first rail is formed via a thickness of the attachment board to connect the attachment in the upright orientation and the second rail extends from a lower or outer surface of the attachment board to connect the attachment in the horizontal orientation.

14. The assembly of claim 11 further comprising a third tongue or groove attachment feature on the attachment having a width dimension and a length dimension larger than the width dimension, the length dimension extending along one of the longitudinal edges of the attachment wherein the second tongue or groove attachment feature supports the attachment board in a first horizontal orientation with the at least one cross edge extending alongside an outer edge of the base board and the third tongue or groove attachment feature supports the attachment board in a second horizontal orientation different from the first orientation with the at least one longitudinal edge extending alongside the outer edge of the base board.

15. The assembly of claim 11 wherein the attachment includes a front arm extension angled relative to the attachment board and the front arm extension includes an inner surface and an outer surface and a thickness between the inner and outer surfaces and a height dimension between a top edge and a bottom edge and the bottom edge of the front arm extension is elevated from a bottom edge of the attachment board to provide clearance for a patient's body.

\* \* \* \* \*